United States Patent [19]
Tyagi et al.

[11] Patent Number: 6,037,130
[45] Date of Patent: *Mar. 14, 2000

[54] WAVELENGTH-SHIFTING PROBES AND PRIMERS AND THEIR USE IN ASSAYS AND KITS

[75] Inventors: Sanjay Tyagi, New York; Fred R. Kramer, Riverdale; Salvatore A. E. Marras, Brooklyn, all of N.Y.

[73] Assignee: The Public Health Institute of the City of New York, Inc., New York, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 09/123,764

[22] Filed: Jul. 28, 1998

[51] Int. Cl.[7] .................................................... C12Q 1/68
[52] U.S. Cl. ........................ 435/6; 436/501; 536/22.1; 536/23.1; 536/24.31; 536/24.32; 536/24.33
[58] Field of Search ................... 435/6, 810, 91.1, 435/91.2; 436/501; 536/22.1, 23.1, 24.1–24.33, 25.3; 935/77, 78

[56] References Cited

U.S. PATENT DOCUMENTS

| | | | |
|---|---|---|---|
| 4,261,968 | 4/1981 | Ullman et al. | 424/8 |
| 4,725,536 | 2/1988 | Fritsch et al. | 435/6 |
| 4,725,537 | 2/1988 | Fritsch et al. | 435/6 |
| 4,752,566 | 6/1988 | Collins et al. | 435/6 |
| 4,766,062 | 8/1988 | Diamond et al. | 435/6 |
| 4,822,733 | 4/1989 | Morrison | 435/6 |
| 5,082,830 | 1/1992 | Brakel et al. | 514/44 |
| 5,118,801 | 6/1992 | Lizardi et al. | 536/27 |
| 5,210,015 | 5/1993 | Gelfand et al. | 435/6 |
| 5,241,060 | 8/1993 | Engelhardt et al. | 536/27 |
| 5,260,433 | 11/1993 | Engelhardt et al. | 536/23 |
| 5,312,921 | 5/1994 | Glazer et al. | 546/108 |
| 5,332,659 | 7/1994 | Kidwell | 435/6 |
| 5,348,853 | 9/1994 | Wang et al. | 435/6 |
| 5,487,972 | 1/1996 | Gelfand et al. | 435/6 |
| 5,491,063 | 2/1996 | Fisher et al. | 435/6 |
| 5,532,129 | 7/1996 | Heller | 435/6 |
| 5,538,848 | 7/1996 | Livak et al. | 435/5 |
| 5,565,322 | 10/1996 | Heller | 435/6 |
| 5,571,673 | 11/1996 | Picone | 435/6 |
| 5,622,821 | 4/1997 | Selvin et al. | 435/6 |

FOREIGN PATENT DOCUMENTS

| | | |
|---|---|---|
| B-57754/86 | 11/1986 | Australia . |
| 0 070 685 A2 | 1/1983 | European Pat. Off. . |
| 0 232 967 A2 | 8/1987 | European Pat. Off. . |
| 0 286 898 A3 | 10/1988 | European Pat. Off. . |
| 0 364 255 A2 | 4/1990 | European Pat. Off. . |
| 0 601 889 A2 | 6/1994 | European Pat. Off. . |
| 0 640 828 A1 | 3/1995 | European Pat. Off. . |
| 0 745 690 A2 | 12/1996 | European Pat. Off. . |
| 5-123195 | 5/1993 | Japan . |
| WO 91/13897 | 9/1991 | WIPO . |
| WO 94/17397 | 10/1994 | WIPO . |
| WO 95/13399 | 5/1995 | WIPO . |
| WO 95/21266 | 10/1995 | WIPO . |
| WO 96/04405 | 2/1996 | WIPO . |
| WO 97/11084 | 3/1997 | WIPO . |
| WO 97/39008 | 10/1997 | WIPO . |

OTHER PUBLICATIONS

M.E. DePecol, et al., "Syntheses, Properties, And Use Of Fluorescent N–(5'–Phospho–4'–Pyridoxyl) Amines In Assay Of Pyridoxamine (Pyridoxine) 5'–Phosphate Oxidase," Analytical Biochemistry 101: 435–441 (1980).

(List continued on next page.)

*Primary Examiner*—Ardin H. Marschel
*Attorney, Agent, or Firm*—Fish & Richardson P.C.

[57] ABSTRACT

Hairpin-forming oligonucleotide probes and primers triple-labeled with a pair of florophores, a shorter wavelength harvester and a longer wavelength emitter, and a quencher. When the probes and primers are stimulated by light that excites the harvester, opening causes an increase in fluorescence by the emitter, while fluorescence from the harvester is continually suppressed. The probes and primers may be used for detection of nucleic acid targets in assays, including amplification assays. Assay kits are provided.

50 Claims, 9 Drawing Sheets

OTHER PUBLICATIONS

H.A. Erlich, et al., "Recent Advances In The Polymerase Chain Reaction," Science 252: 1643–1651 (1991).

D. Gillespie, et al., "A Quantitative Assay For DNA–RNA Hybrids With DNA Immobilized On A Membrane," J. Mol. Biol. 12: 829–842 (1965).

Z. Guo, et al., "Enhanced Discrimination Of Single Nucleotide Polymorphisms By Artificial Mismatch Hybridization," Nature Biotechnology 15: 331–335 (1997).

R.P. Haugland, et al., "Dependence Of The Kinetics Of Singlet–Singlet Energy Transfer On Spectral Overlap," P.N.A.S. (U.S.A.) 63: 23–30 (1969).

P.M. Holland, et al., "Detection Of Specific Polymerase Chain Reaction Product By Utilizing the 5'–3' Exonuclease Activity Of Thermus Aquaticus DNA Polymerase," P.N.A.S. (U.S.A.) 88: 7276–7280 (1991).

P.M. Holland, et al., "Detection Of Specific Polymerase Chain Reaction Product By Utilizing the 5'–3' Exonuclease Activity Of Thermus Aquaticus DNA Polymerase," Clinical Chemistry 38: 462–463 (1992).

E.N. Hudson, et al., "Synthesis And Characterization Of Two Fluorescent Sulfhydryl Reagents," Biochemistry 12: 4154–4161 (1973).

V.M. Ingram, "Gene Mutations In Human Haemoglobin: The Chemical Difference Between Normal And Sickle Cell Haemoglobin," Nature 180: 326–328 (1957).

U. Landegren, et al., " A Ligase–Mediated Gene Detection Technique," Science 241: 1077–1080 (1988).

R. Lathe, "Synthetic Oligonucleotide Probes Deduced From Amino Acid Sequence Data, Theoretical And Practical Considerations," J. Mol. Biol. 183: 1–12 (1985).

L.G. Lee, et al., "Allelic Discrimination By Nick–Translation PCR With Fluorogenic Probes," Nucleic Acid Research 21: 3761–3766 (1993).

P. Lichter, et al., "High–Resolution Mapping Of Human Chromosome 11 By In Situ Hybridization With Cosmid Clones," Science 247: 64–69 (1990).

K.J. Livak, et al., "Towards Fully Automated Genome–Wide Polymorphism Screening," Nature Genetics 9: 341–342 (1995).

H. Lomell, et al., "Quantitative Assays Based On The Use Of Replicatable Hybridization Probes," Clinical Chemistry 35: 1826–1831 (1989).

E.D. Matayoshi, et al., "Novel Fluorogenic Substrates For Assaying Retroviral Proteases By Resonance Energy Transfer," Science 247: 954–958 (1990).

J.A. Matthews, et al., "Analytical Strategies For The Use Of DNA Probes," Analytical Biochemistry 169: 1–25 (1988).

L.E. Morrison, et al., "Sensitive Fluorescence–Based Thermodynamic And Kinetic Measurements Of DNA Hybridization In Solution," Biochemistry 32: 3095–3104 (1993).

L.E. Morrison, et al., "Solution–Phase Detection Of Polynucleotides Using Interacting Fluorescent Labels And Competitive Hybridization," Analytical Biochemistry 183: 231–244 (1989).

N.C. Nelson, et al., "Detection Of All Single–Base Mismatches In Solution By Chemiluminescence," Nucleic Acid Research 24: 4998–5003 (1996).

P.S. Nelson, et al., "Bifunctional Oligonucleotide Probes Synthesized Using A Novel CPG Support Are Able To Detect Single Base Pair Mutations," Nucleic Acids Research 17: 7187–7194 (1989).

Newton, et al., Analysis Of Any Point Mutation In DNA. The Amplification Refractory Mutation System (ARMS) Nucleic Acids Research 17: 2503–2516 (1989).

M. Orita, et al., "Detection Of Polymorphisms Of Human DNA By Gel Electrophoresis As Single–Strand Conformation Polymorphism" P.N.A.S. (U.S.A.) 86: 2766–2770 (1989).

H. Orum, et al., "Single Base Pair Mutation Analysis By PNA Directed PCR Clamping," Nucleic Acids Research 21: 5332–5336 (1993).

R.K. Saiki, et al., "Genetic Analysis Of Amplified DNA With Immobilized Sequence–Specific Oligonucleotide Probes," P.N.A.S. (U.S.A.) 86: 6230–6234 (1989).

P.R. Selvin, "Fluorescence Resonance Energy Transfer," Methods in Enzymology 246: 300–335 (1995).

D. Shore, et al., "DNA Flexibility Studied By Covalent Closure Of Short Fragments Into Circles," P.N.A.S. (U.S.A.) 78: 4833–4837 (1981).

S. Sixou, et al., " Intracellular Oligonucleotide Hybridization Detected By Fluorescence Resonance Energy Transfer," Nucleic Acids Research 22: 662–668 (1994).

L. Stryer, "Fluorescence Energy Transfer As A Spectroscopic Ruler," Ann. Rev. Biochem. 47: 819–846 (1978).

N. Tibanyenda, et al., The Effect Of Single Base–Pair Mismatches On The Duplex Stability Of d(T–A–T–T–A–A–T–A–T–C–A–A–G–T–T–G) • d(C–A–A–C–T–T–G–A–T–A–T–T–A–A–T–A), Eur. J. Biochem. 139: 19–27 (1984).

S. Tyagi, et al., Molecular Beacons: Probes That Fluoresce Upon Hybridization, Nature Biotechnology 14: 303–308 (1996).

E.F. Ullman, et al., "Fluorescent Excitation Transfer Immunoassay," The Journal of Biological Chemistry 251: 4172–4178 (1976).

G.T. Walker, et al., Strand Displacement Amplification—An Isothermal, In Vitro DNA Amplification Technique Nucleic Acids Research 20: 1691–1696 (1992).

G.T. Wang, et al., "Design And Synthesis Of New Fluorogenic HIV Protease Substrates Based On Resonanc Energy Transfer," Tetrahedron Letters 31: 6493–6496 (1990).

H. Werntges, et al., "Mismatches In DNA Double Strands: Thermodynamic Parameters And Their Correlation To Repair Efficiencies," Nucleic Acids Research 14: 3773–3790 (1986).

S.J. Wood, "DNA–DNA Hybridization In Real Time Using BIAcore," Microchemical Journal 47: 330–337 (1993).

C. Yang et al., "Studies Of Transfer RNA Tertiary Structure By Singlet–Singlet Energy Transfer," P.N.A.S. (U.S.A.) 71: 2838–2842 (1974).

R. Youil et al., "Screening For Mutations By Enzyme Mismatch Cleavage With T4 Endonuclease," VII.P.N.A.S (U.S.A.) 92: 87–91 (1995).

Su–Chun Hung et al., "Cyanine Dyes with High Absorption Cross Section as Donor Chromophores in Energy Transfer Primers," Analytical Biochemistry 243:15–27 (1996).

Jingyue Ju et al., "Design and Synthesis of Flourescence Energy Transfer Dye–Labeled Primers and Their Application for DNA Sequencing and Analysis," Analytical Biochemistry 231: 131–140 (1995).

Jingyue Ju et al., "Fluorescence energy transfer dye–labeled primers for DNA sequencing and analysis," Proc. Natl. Acad. Sci. USA, 92:4347–4351, May (1995).

Leondios G. Kostrikis et al. "Spectral Genotyping of Human Alleles," Science 279:1228–1229 (1998).

L. G. Lee et al., "New energy transfer dyes for DNA sequencing," Nucleic Acids Research 25(14):2816–2822 (1997).

A. Nazarenko et al., "A closed tube format for amplification and detection of DNA based on energy transfer," Nucleic Acids Research 25(12):2516–2521 (1997).

Amy S. Piatek et al., "Molecular beacon sequence analysis for detecting drug resistance in Mycobacterium tuberculosis," Nature Biotechnology 16:359–363 (1998).

Sanjay Tyagi et al., "Multicolor molecular beacons for allele discrimination," Nature Biotechnology, 16:49–53 (1998).

B.C. Bagwell, et al., "A New Homogeneous Assay System For Specific Nucleic Acid Sequences: Poly–dA And Poly–A Detection," Nucleic Acids Research 22: 2424–2425 (1994).

J. Brand, et al., "Fluorescence Probes For Structure," Ann Rev Biochemistry 41: 843–868 (1972).

K.J. Breslauer, et al., "Predicting DNA Duplex Stability From The Base Sequence," P.N.A.S. (U.S.A.) 83: 3746–3750 (1986).

C.R. Cantor, et al., "Techniques For The Study Of Biological Structure And Function," (W.H. Freeman and Co., San Francisco) (U.S.A.) pp. 448–455 (1980).

C.R. Cantor, "Lighting Up Hybridization," Nature Biotechnology 14: 264 (1996).

Cardullo, et al., "Detection Of Nucleic Acid Hybridization By Nonradiative Fluorescence Resonance Energy Transfer," P.N.A.S. (U.S.A.) 85: 8790–8794 (1988).

A. Coghlan, "Brilliant Beacons Colour–Code Genes," New Scientist p. 24 (Mar. 16, 1996).

B.A. Connolly, et al., "Chemical Synthesis Of Oligonucleotides Containing A Free Sulphydryl Group And Subsequent Attachment Of Thiol Specific Probes," Nucleic Acids Research 13: 4485–4502, 1985.

J.P. Cooper, et al., "Analysis Of Fluorescence Energy Transfer In Duplex And Branched DNA Molecules," Biochemistry 29: 9261–9268 (1990).

Parkhurst et al., 37th Annual Meeting of the Biophysical Society, Washington, DC., Abstract W–Pos 97 (1993).

Sambrook et al., *"Molecular Cloning"* A Laboratory Manual, pp. 11.47 and 11.55–11.57 (1989)

Sixou et al., 37th Annual Meeting of the Biophysical Society, Washington, DC, Abstract Tu–Pos 351 (1993)

SEQUENCE LISTING

<160> NUMBER OF SEQ ID NOS: 13

<210> SEQ ID NO 1
<211> LENGTH: 30
<212> TYPE: DNA
<213> ORGANISM: Artificial Sequence
<220> FEATURE:
<223> OTHER INFORMATION: Synthetically generated

<400> SEQUENCE: 1
tttttccacg cttgtgggtc aacccgtgg                                    30

<210> SEQ ID NO 2
<211> LENGTH: 33
<212> TYPE: DNA
<213> ORGANISM: Artificial Sequence
<220> FEATURE:
<223> OTHER INFORMATION: Synthetically generated

<400> SEQUENCE: 2
tttttccacg cttgtgggtc aacccgtgg ttt                                33

<210> SEQ ID NO 3
<211> LENGTH: 27
<212> TYPE: DNA
<213> ORGANISM: Artificial Sequence
<220> FEATURE:
<223> OTHER INFORMATION: Synthetically generated

<400> SEQUENCE: 3
ccacgttctt gtgggtcaac cccgtgg                                      27

<210> SEQ ID NO 4
<211> LENGTH: 29
<212> TYPE: DNA
<213> ORGANISM: Artificial Sequence
<220> FEATURE:
<223> OTHER INFORMATION: Synthetically generated

<400> SEQUENCE: 4
ccggtccgct tgtgggtcaa cccgaccgg                                    29

<210> SEQ ID NO 5
<211> LENGTH: 31
<212> TYPE: DNA
<213> ORGANISM: Artificial Sequence

```
<220> FEATURE:
<223> OTHER INFORMATION: Synthetically generated

<400> SEQUENCE: 5
ttcctggccg cttgtgggtc aacccgccag g                              31

<210> SEQ ID NO 6
<211> LENGTH: 33
<212> TYPE: DNA
<213> ORGANISM: Artificial Sequence
<220> FEATURE:
<223> OTHER INFORMATION: Synthetically generated

<400> SEQUENCE: 6
tttttgcggc cgcttgtggg tcaacccgcc gca                            33

<210> SEQ ID NO 7
<211> LENGTH: 34
<212> TYPE: DNA
<213> ORGANISM: Artificial Sequence
<220> FEATURE:
<223> OTHER INFORMATION: Synthetically generated

<400> SEQUENCE: 7
cacacgtcct gccgcttgtg ggtcaacccg cagg                           34

<210> SEQ ID NO 8
<211> LENGTH: 36
<212> TYPE: DNA
<213> ORGANISM: Artificial Sequence
<220> FEATURE:
<223> OTHER INFORMATION: Synthetically generated

<400> SEQUENCE: 8
cagcacacgt cgcgcgcttg tgggtcaacc ccgcga                         36

<210> SEQ ID NO 9
<211> LENGTH: 37
<212> TYPE: DNA
<213> ORGANISM: Artificial Sequence
<220> FEATURE:
<223> OTHER INFORMATION: Synthetically generated

<400> SEQUENCE: 9
tcagcacacg tcgcgcgctt gtgggtcaac cccgcga                        37

<210> SEQ ID NO 10
<211> LENGTH: 25
<212> TYPE: DNA
<213> ORGANISM: Artificial Sequence
<220> FEATURE:
<223> OTHER INFORMATION: Synthetically generated

<400> SEQUENCE: 10
ccacgcttgt gggtcaaccc cgtgg                                     25

<210> SEQ ID NO 11
<211> LENGTH: 25
<212> TYPE: DNA
<213> ORGANISM: Artificial Sequence
<220> FEATURE:
<223> OTHER INFORMATION: Synthetically generated

<400> SEQUENCE: 11
ccacgcttgt cggtcaaccc cgtgg                                     25
```

-continued

```
<210> SEQ ID NO 12
<211> LENGTH: 32
<212> TYPE: DNA
<213> ORGANISM: Artificial Sequence
<220> FEATURE:
<223> OTHER INFORMATION: Synthetically generated

<400> SEQUENCE: 12
caccttcacc ctcagaaggt gaccaagttc at                                    32

<210> SEQ ID NO 13
<211> LENGTH: 36
<212> TYPE: DNA
<213> ORGANISM: Artificial Sequence
<220> FEATURE:
<223> OTHER INFORMATION: Synthetically generated

<400> SEQUENCE: 13 ttttcacct tcaccctaga aggtgaccaa gttcat                                36
```

WAVELENGTH-SHIFTING PROBES AND PRIMERS AND THEIR USE IN ASSAYS AND KITS

STATEMENT AS TO FEDERALLY SPONSORED RESEARCH

Some work on this invention was carried out under National Institutes of Health Grant HL-43521. The United States Government may have certain rights in this invention.

This invention relates to nucleic acid hybridization probes and amplification primers, and to kits and assays employing them.

BACKGROUND OF THE INVENTION

Hairpin-forming oligonucleotide hybridization probes with interactive label pairs, particularly fluorescent label pairs and fluorescer-quencher label pairs, are known. Tyagi et al., PCT application No. WO95/13399; Tyagi et al., PCT application No. WO97/39008; Tyagi and Kramer (1996) Nature Biotechnology 14:303. Preferred embodiments of these probes, labeled with a fluorophore and a quencher, are "dark", that is, have relatively little or no fluorescence, when free in solution but fluoresce when hybridized to their nucleic acid targets. We refer to such embodiments as "molecular beacon probes." They are constructed with a variety of fluorophores and are utilized in both end-point and real-time homogeneous assays, including multiplex assays. Tyagi et al. (1998) Nature Biotechnology 16:49; Kostrikis et al. (1998) Science 279:1228; Piatek et al. (1998) Nature Biotechnology 16:359. Hairpin-containing primers similarly labeled with a fluorophore and a quencher are also known. Nazarenko et al. (1997) Nucleic Acids Research 25:2516.

Fluorescence assay instruments that operate with a single stimulation wavelength are much less complicated and much less expensive than instruments that operate with multiple stimulation wavelengths. Almost all assay instruments, including sophisticated instruments costing many tens of thousands of dollars (U.S.) operate with single wavelength stimulation, even if the wavelength is selectable. Because every fluorophore has an optimal excitation wavelength, the choice of fluorophores to be used with a detection instrument having such a light source is limited. Certain fluorophores will be excited poorly or essentially not at all by the source. Red fluorophores such as tetramethylrhodamine (TMR) and Texas red are only minimally excited by a blue light source. A sophisticated, expensive instrument such as the Applied BioSystems 7700 PRISM, can detect fluorescence from TMR stimulated by a blue light source, but not Texas red. Less sophisticated, less expensive instruments can detect neither one. In multiplex assays for multiple targets using multiple hairpin probes or primers having differently colored fluorophores, it is desirable to be able to use four or even more fluorophores whose emission spectra have limited overlap, but the choice of fluorophores is limited by the use of single wavelength stimulation. Also, multiplex assays suffer from the drawback that the emission intensities of some of the fluorophores are very small both in absolute terms and also relative to other fluorophores in the assay. Furthermore, because the Stokes shift (the wavelength difference between the optimal excitation wavelength and optimal emission wavelength) of fluorophores is generally only a few nanometers, hairpin probes and primers whose fluorophores have emission maxima at or very close to the wavelength of the excitation source tend to suffer from background signal resulting from the source itself being detected by the fluorometer. This tends to be more pronounced when less expensive, unsophisticated detectors are employed.

An aspect of the present invention is probes and primers whose conformational change produces a detectable fluorescent signal having a greater Stokes shift than conventional hairpin probes and primers.

Another aspect of the present invention is a wider range of hairpin-forming probes and primers that are effectively quenched ("dark") in the absence of target but are better excited in the presence of target by a monochromatic light source.

Another aspect of the present invention is a group, or series, of hairpin-forming probes or primers containing differently colored fluorophores, all of which can be reasonably well excited by a single monochromatic light source.

Another aspect of the present invention is additional probes and primers suitable for use with single-wavelength stimulation instruments, including unsophisticated instruments for which the current choices are extremely limited.

Another aspect of the present invention is hairpin-forming probes and primers having reduced background signal as a consequence of the source itself not being detected.

Another aspect of the present invention is probes that fluoresce in one color if hybridized to target but change color if digested by a nuclease.

Additional aspects of the invention will be apparent from the description, including the claims, which follows.

SUMMARY OF THE INVENTION

We have discovered that hairpin-forming probes and primers may be constructed such that their fluorescence when closed is suppressed, but when open, they are well excited by a monochromatic light source and emit strongly at a wavelength distanced from the wavelength of the source. Certain preferred embodiments are "dark" when closed, by which we mean that their total fluorescence when closed is less than twenty percent of their total fluorescence when open and that they do not change color upon opening. Probes according to this invention are suitable for use in end-point detection assays, and probes and primers according to this invention are suitable for use in real-time amplification assays such as, for example, polymerase chain reaction (PCR) assays. The end-point assays and real-time assays may be multiplex assays. Assay kits containing the probes and primers are also provided.

This invention includes hairpin-forming nucleic acid hybridization probes and primers comprising:

a) a hairpin-forming oligonucleotide sequence;
 b) a fluorescent emitter moiety attached to said oligonucleotide sequence, said emitter moiety having an excitation spectrum and an emission spectrum having a maximum emission wavelength;
 c) a fluorescent harvester moiety attached to said oligonucleotide sequence, said harvester moiety having an excitation spectrum having a maximum excitation wavelength, having an emission spectrum that overlaps the excitation spectrum of the emitter moiety and having a maximum emission wavelength, the emission of the harvester moiety at its maximum emission wavelength having a first magnitude when said harvester moiety is unquenched and stimulated at its maximum excitation wavelength; and
 d) a quencher moiety capable of quenching the fluorescence of at least one of the emitter moiety and the harvester moiety, said oligonucleotide having a closed conformation wherein said quencher moiety is in a quenching relationship to at least one of said harvester and emitter moieties and wherein, when excited at the maximum excitation wavelength of the harvester moiety, emission at the maximum emission wavelength of the harvester moiety is suppressed relative to said first magnitude, and emission at the maximum emission wavelength of the emitter moiety has a second magnitude, and said oligonucleotide having an open conformation, not including said stem duplex, in which said quencher moiety is not in a quenching relationship with said harvester moiety or said emitter moiety wherein, when excited at the maximum excitation wavelength of the harvester moiety, emission at the maximum emission wavelength of the harvester moiety is suppressed relative to said first magnitude, energy is transferred from the harvester moiety to the emitter moiety, and emission at the maximum emission wavelength of the emitter moiety is detectably greater than said second magnitude.

For molecular beacon probes modified according to this invention, hybridization of the probes to target strands causes the probes to shift from their closed conformation to their open conformation.

Unless otherwise defined, all technical and scientific terms used herein have the same meaning as commonly understood by persons of ordinary skill in the art to which this invention belongs. Although methods and materials similar or equivalent to those described herein can be used in the practice or testing of the present invention, suitable methods and materials are described below. All publications, patents and patent applications referred to herein are incorporated by reference in their entirety. In case of conflict, the present application, including definitions will control. In addition, the materials, methods and examples described herein are illustrative only and not intended to be limiting.

DETAILED DESCRIPTION

Figure 1:
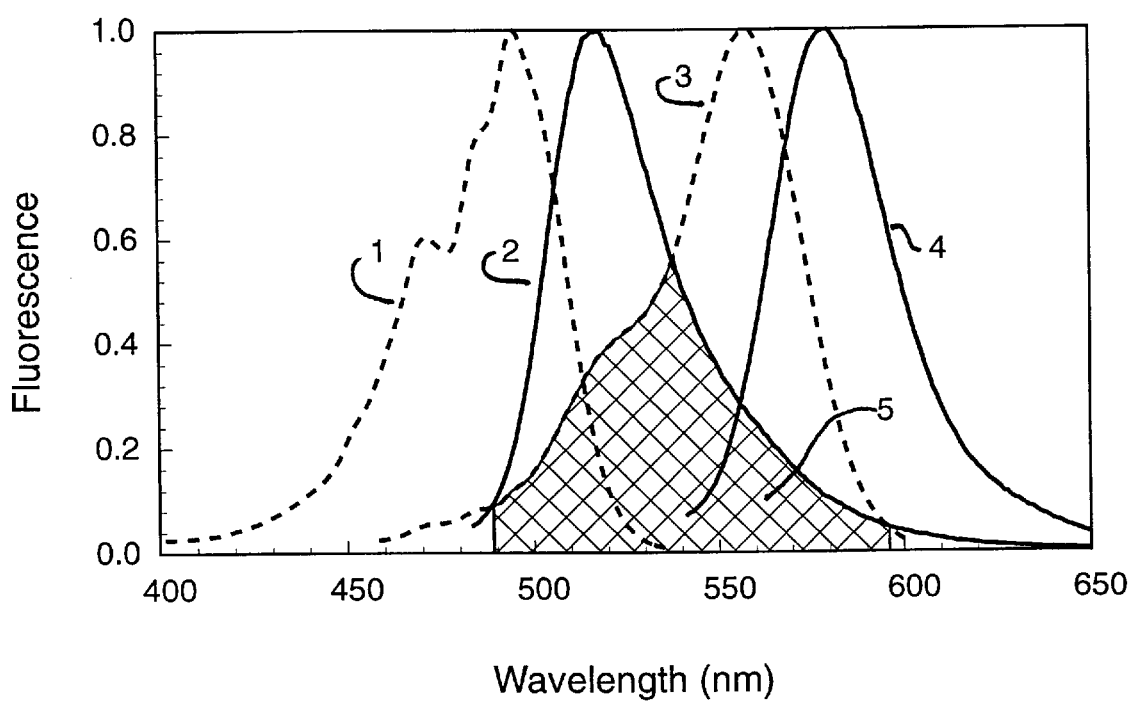
FIG. 1 is a graph of absorbance and emission spectra of two fluorophores, fluorescein and tetramethylrhodamine (TMR).

Hairpin-forming oligonucleotide probes, including molecular beacon probes, that may be modified according to this invention are interactively labeled, hairpin-forming oligonucleotides comprising a stem-and-loop structure. The loop contains a probe sequence complementary to the probe's target. Nucleotide sequences ("arms") flank the probe sequence, and a sequence in one arm is complementary to a sequence in the other arm. When the probe is not hybridized to target, the arms hybridize with one another to form a stem hybrid, which is sometimes referred to as the "stem duplex". This is the closed conformation. When the probe hybridizes to its target, the longer and stronger probe-target hybrid overcomes the stem hybrid and separates the arm sequences. This is the open conformation. In the open conformation an arm may also hybridize to the target. Molecular beacon probes may be free in solution, or they may be tethered to a solid surface. For some molecular beacon probes, which we refer to as "allele-discriminating," only perfectly complementary strands are targets that cause this change under assay conditions; for other embodiments the probe will open despite the presence of one or a few internal mismatches with the target. Molecular beacon probes have a fluorophore attached to one arm and a quencher attached to the other arm. When the arms form a stem, the quencher is very close to the fluorophore and effectively quenches or suppresses its fluorescence, rendering the probe dark. Such probes are described in copending U.S. patent applications Ser. No. 08/439,619 and Ser. No. 08/990,176, both of which are incorporated by reference herein in their entirety. The fluorophore and quencher, for example, tetramethylrhodamine and DABCYL, need not be a FRET pair.

The oligonucleotide sequences of molecular beacon probes modified according to this invention may be DNA, RNA, peptide nucleic acid (PNA) or combinations thereof. Modified nucleotides may be included, for example nitropyrole-based nucleotides or 2'-O-methylribonucleotides. Modified linkages also may be included, for example phosphorothioates. Modified nucleotides and modified linkages may also be incorporated in wavelength-shifting primers according to this invention, subject, as will be recognized, to the requirement that one arm be able to serve a primer for a nucleic acid polymerase.

For probes according to this invention, the length of the loop sequence that is target complementary, the length of the stem hybrid and the relation of the two is designed according to the assay conditions for which the probe is to be utilized. Lengths of target-complement sequence and stem hybrid for particular assay conditions can be estimated by known means, tried and adjusted, if necessary. Typical probe sequences for use in PCR assays are in the range of 16 to 25 nucleotides. Typical stem lengths are in the range of 3 to 8, more commonly 4 to 7 nucleotides. The strength of the stem hybrid is adjusted by routine experimentation to achieve proper functioning. In addition to length, the strength of the stem hybrid can be adjusted by altering the G-C content and insertion of destabilizing mismatches, as will be appreciated. One arm can be designed to be partially or completely complementary to the target. If the 3' arm is complementary to the target the probe can serve as a primer for a DNA polymerase. Also, wavelength-shifting molecular beacon probes can be immobilized to solid surfaces, as by tethering, as well as being free-floating.

A wide range of fluorophores may be used in probes and primers according to this invention. Available fluorophores include coumarin, fluorescein, tetrachlorofluorescein, hexachlorofluorescein, Lucifer yellow, rhodamine, BODIPY, tetramethylrhodamine, Cy3, Cy5, Cy7, eosine, Texas red and ROX. Combination fluorophores such as fluorescein-rhodamine dimers, described, for example, by Lee et al. (1997), Nucleic Acids Research 25:2816, are also suitable. Fluorophores may be chosen to absorb and emit in the visible spectrum or outside the visible spectrum, such as in the ultraviolet or infrared ranges.

A quencher is a moiety that, when placed very close to an excited fluorophore, causes there to be little or no fluorescence. Suitable quenchers described in the art include particularly DABCYL and variants thereof, such as DABSYL, DABMI and Methyl Red. Fluorophores can also be used as quenchers, because they tend to quench fluorescence when touching certain other fluorophores. Our preferred quenchers are either chromophores such as DABCYL or malachite green, or fluorophores that do not fluoresce in the detection range when the probe is in the open conformation.

Hairpin-forming probes according to this invention may be utilized in detection assays. They may also be used as detectors in amplifications assays, and may be added prior to amplification, in which case quantitative results as to the initial concentration of amplifiable target may be obtained. Amplification reactions include the polymerase chain reaction (PCR), strand displacement amplification (SDA), nucleic acid sequence based amplification (NASBA), transcription mediated amplification (TMA), the ligase chain reaction (LCR), rolling circle amplification, and RNA-directed RNA amplification catalyzed by an enzyme such as Q-beta replicase. Multiple probes for multiple targets may be used in a single reaction tube or other container for multiplex assays.

Hairpin-forming primers are used in those of the amplification reactions identified above that include one or more primers. They may be modified according to the present invention have an arm sequence that binds to a nucleic acid target, such that the hairpin-containing primer can be extended by incubation with a nucleic acid polymerase. The loop portion may, but need not be, complementary to the original target strand. Hairpin-containing primers have a stem labeled with a fluorophore on one arm and a quencher on the other arm, similarly to molecular beacon detection probes. Embodiments of the instant invention will be described primarily in connection with molecular beacon detection probes. Workers in the art will understand that the concepts and teachings apply to hairpin primers as well, and will understand how to apply the concepts and particular teachings to hairpin-containing primers.

FIG. 1 shows the excitation and emission spectra of two fluorophores, fluorescein and tetramethylrhodamine (TMR). Fluorescein has an absorption spectrum 1 with a maximum at 490 nm and an emission spectrum 2 with a maximum at 515 nm. Fluorescein has a Stokes Shift, the difference between the two maxima, of 25 nm. TMR has an excitation spectrum 3 with a maximum at 555 nm and an emission spectrum 4 with a maximum at 575 nm. It has a Stokes shift of 20 nm.

FIG. 1 shows the relatively small Stokes shift typical of most fluorophores. An instrument producing a stimulation light at a nominal wavelength of, for example, 488 nm, may in fact have an excitation spectrum that includes longer wavelengths, and a detector set for 515 nm may in fact respond to light that includes shorter wavelengths. The fluorescent signal measured by such an instrument would include a background reading from the stimulating light.

Figure 2:
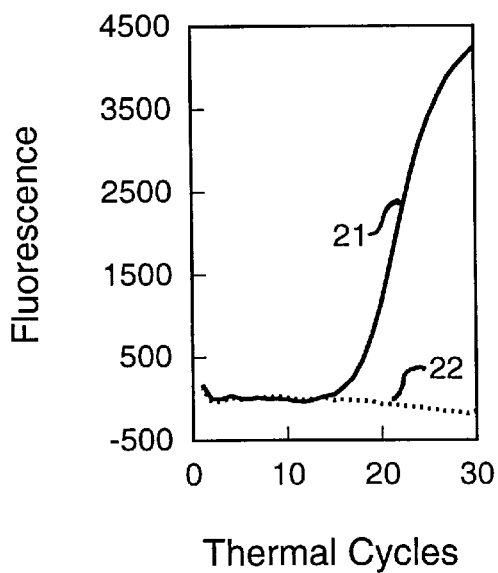
FIG. 2 is a graph of fluorescence of a conventional fluorescein-containing molecular beacon probe during PCR thermal cycling.
Figure 3:
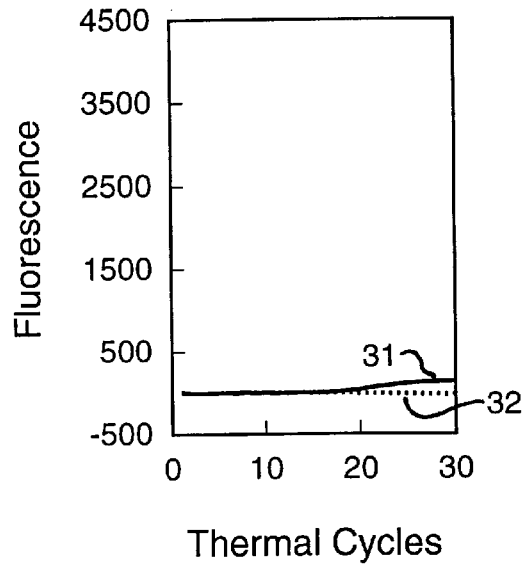
FIG. 3 is a graph of fluorescence of a conventional Texas red-containing molecular beacon probe during PCR thermal cycling.

FIG. 1 also shows why there is a serious practical limitation of an instrument having a single stimulating wavelength. If the stimulating wavelength is 490 nm, which is optimum for the excitation of fluorescein, a molecular beacon probe having TMR as the fluorophore would be stimulated only ten percent as well as it would have been by a source at 560 nm. The intensity of its emission would be correspondingly lower. If the excitation source were changed to 560 nm, which is appropriate for TMR, fluorescein would not be excited at all. Thus, the number of different fluorophores that work well is restricted no matter which excitation wavelength is utilized. These effects are illustrated in FIG. 2 and FIG. 3, which present the results of using a conventional molecular beacon probe design as a detector for amplicons in a PCR amplification reaction. The probe design includes a stem-and-loop hairpin structure that is terminally labeled with a fluorophore and the quencher DABCYL oppositely positioned across the stem duplex. FIG. 2 shows what happens when the fluorophore is fluorescein, the excitation source is a blue argon laser (488 nm), and the detector measures fluorescence in the emission range of fluorescein. Fluorescence intensities reported in FIG. 2, and also in FIG. 3 and FIG. 4, were obtained using an Applied Biosystems 7700 PRISM spectrofluorometric thermal cycler (The Perkin-Elmer Corporation), which has sophisticated fluorescence measuring. The fluorescence intensity 21 of a sample containing target molecules increased above the fluorescence intensity 22 of a sample containing no target molecules beginning at about PCR cycle 15 and increased rapidly to a difference of about 4000 units by cycle 30. FIG. 3 shows what happens in a parallel experiment in which the only differences are that the fluorophore of the molecular beacon probe is Texas red instead of fluorescein, and the detector measures fluorescence in the emission range of Texas red. Here again the fluorescence intensity 31 of the sample containing target began to deviate from the fluorescence intensity 32 of the targetless control at about cycle 15, but by cycle 30 the difference was only about 200 units as compared to 4000 seen with the molecular beacon probe containing fluorescein. Texas red is not a useful fluorophore when the stimulating source emits blue light, even with an expensive instrument that has sophisticated fluorescence measurement.

Figure 4:
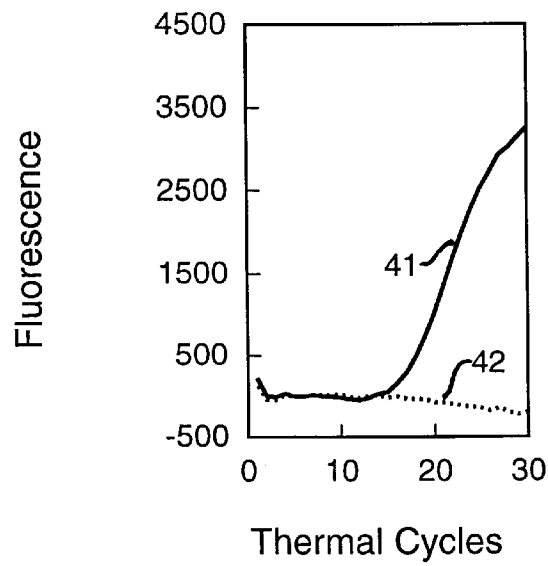
FIG. 4 is a graph of fluorescence of a Texas red-containing wavelength-shifting molecular beacon probe according to this invention during PCR thermal cycling.

FIG. 4 shows the results of a third parallel experiment in which the only difference from the second experiment was that the Texas red probe of FIG. 3 was changed to a construction according to the instant invention. Here again the fluorescence intensity 41 of the sample containing target began to deviate from the reading 42 of the targetless control at approximately cycle 15, but by cycle 30 the difference was approximately 3000 units, about seventy-five percent of the magnitude of the fluorescence intensity of the fluorescein-labeled conventional molecular beacon probe utilized in the experiment shown in FIG. 2 and about fifteen times as great as the magnitude of the fluorescence intensity of the conventional molecular beacon probe labeled with Texas red, shown in FIG. 3. This increase was achieved without sacrificing the property that the probe itself is essentially dark when not hybridized to target as fluorescence intensity 42 shows. Thus, an excitation source at 488 nm is an acceptable source for a Texas red probe according to this invention and, conversely, Texas Red is an acceptable fluorophore for probes and primers according to this invention for use with an excitation source at 488 nm. The emission intensity achieved by the probe according to this invention makes the probe suitable for use not only with sophisticated detection such as the Applied Biosystems PRISM, but also for use with less expensive instruments that have unsophisticated fluorescence measurement.

Figure 5:
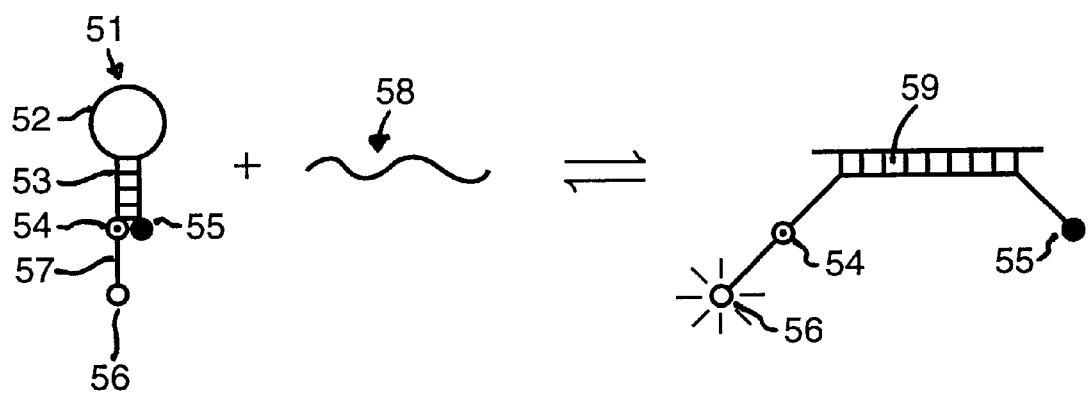
FIG. 5 is a schematic representation of the interaction of a preferred probe of this invention with its target.

The structure and operation of modified molecular beacon probes and hairpin primers according to this invention will be explained by reference to a preferred probe embodiment, shown schematically in FIG. 5. Probe 51 includes a molecular beacon probe hairpin oligonucleotide structure, namely, a loop 52, stem duplex 53, a DABCYL quencher 55 on one end and a fluorescein fluorophore 54 opposite the quencher in a close, quenching relationship across the stem hybrid when the probe is in the closed conformation. The probe includes an extension 57 of several nucleotides past the fluorescein. Extension 57 terminates in a nucleotide that is linked to a Texas red fluorophore 56. In the presence of target strand 58, loop 52 forms hybrid 59 with the target strand, unwinding stem 53 and separating the quencher 55 from the fluorescein 54 and Texas red 56. However, in this open conformation the fluorescein acts as a "harvester" moiety that absorbs energy from the excitation source but transfers a significant portion of the energy, in some constructions the great majority of the energy, to the Texas red fluorophore, which acts as an "emitter" moiety by receiving the transferred energy and emitting it at its characteristic, longer wavelength.

The function of probe 51 in the open conformation appears to obey the rules of FRET, which require that the two fluorophores be separated by an appropriate distance and that the emission spectrum of the harvester moiety significantly overlaps the absorption spectrum of the emitter moiety. Referring to FIG. 1, the shaded area 5 depicts such a spectral overlap for the two fluorophores whose spectra are presented there. We have discovered that probe 51 is essentially dark in its closed conformation despite the presence of a second fluorophore that makes a FRET pair with fluorescein. Possibly the combination of fluorescein and DABCYL does not make a FRET pair with Texas red. Whatever the mechanism may be, there is little to no fluorescence at 610 nm when the probe is closed. Similarly, there is little to no fluorescence at 515 nm when the probe is closed.

Probes and primers according to this invention, which we refer to as "wavelength-shifting" molecular beacon probes and "wavelength-shifting" hairpin primers, like their unmodified counterparts, can be made from DNA, RNA, PNA (peptide nucleic acid), or combinations of the foregoing. Modified nucleotides and modified nucleotide linkages may be used in place of naturally occurring nucleotides and linkages. Fluorophores and quenchers can be inserted into the strand in place of a nucleotide. The loop of a wavelength-shifting molecular beacon probe is complementary to the target and has a length of at least seven nucleotides, with a preferred range being from about twelve to about thirty nucleotides, although longer loops can be used. Wavelength-shifting primers may have similar loops; however, their loops need not be complementary to the target, and their loops can be as short as three nucleotides. The arms form a stem duplex of at least three nucleotides with a preferred range being from three to about eight nucleotides, although longer stems are suitable in some applications.

A first arm of the probe or primer is labeled with a quencher. The probe or primer is labeled with a pair of fluorophores capable of interacting by energy transfer when the quencher is relocated distantly by the opening of the probe or primer. One of the pair is attached to the second arm in a close, quenching relationship with the quencher when the probe is closed. Either the shorter wavelength fluorophore, the "harvester", or the longer wavelength fluorophore, the "emitter", has that relationship to the quencher. The other fluorophore may be placed farther away from the quencher. Alternatively, the quencher may be positioned opposite a point on the other arm that is intermediate to the two fluorophores. When the probe is bound to target or the primer is opened, the harvester and the emitter are separated by a distance appropriate for fluorescence energy transfer. The fluorophore that is not in a close, quenching relationship to the quencher across the stem duplex may be attached to the second arm in the region of the stem or an extension outside the stem, or in some cases it may be attached to the loop. In the closed conformation, as stated above, the quencher and one of the harvester and emitter fluorophores is in a close, quenching relationship, by which we mean that they are sufficiently close to one another that quenching predominates over fluorescence resonance energy transfer. Most preferably the two moieties touch each other. However, separation by a single base pair along the stem duplex is almost always satisfactory. Even greater separations are possible in many instances, namely, 2–4 base pairs or even 5–6 base pairs, particularly if a spacer, described below, is utilized. For these greater separations the helical nature of the stem duplex should be considered for its effect on the distance between the moieties.

In embodiments in which the emitter fluorophore is in a close, quenching relationship with the quencher moiety when the probe is closed, the harvester and emitter fluorophore must be at an appropriate FRET distance.

The transfer of energy from the harvester fluorophore to the emitter fluorophore is governed by the rules of fluorescence resonance energy transfer [Stryer (1979) Ann. Rev. Biochem. 47:819], which we use to aid in the design of probes and primers according to this invention. In particular, two rules are considered in order to maximize the efficiency of energy transfer. First, the absorption spectrum of the emitter and the emission spectrum of the harvester must overlap. Second, the two fluorophores must be spaced relative to one another such that they can undergo fluorescence resonance energy transfer (FRET). The optimal distance between the emitter and harvester fluorophores is a function of two opposing effects. On the one hand, the farther apart the two moieties are, the lower the efficiency of energy transfer; the transfer of energy from the exciter to the emitter is proportional to $1/R^6$, where R is the distance between the two fluorophores. On the other hand, the closer they are, the greater the potential for undesirable quenching of the emitter emission. The distance between the two fluorophores as determined by the number of atoms in the chain separating the two fluorophores can be varied in accordance with the nature of the backbone to which they are attached. They should be sufficiently separated so that there is substantial FRET, and preferably they are sufficiently separated that FRET predominates over quenching. These rules are commonly employed in order to optimize the efficiency of energy transfer from one fluorophore to the other when they are attached to a DNA molecule [Ju et al. (1995) Proc. Natl. Acad. Sci. USA 92:4347; Ju et al. (1995) Anal. Biochem. 231:131; Hung et al. (1998) Anal. Biochem. 252:78; Mathies et al. PCT/US96/13134]. Distances of 20–60 Angstroms are appropriate, which translates to about six to about eighteen nucleotides, with seven nucleotides being a preferred separation and the amount of energy transfer decreasing as separation is increased. For example, with fluorescein as the harvester fluorophore, a DABCYL quencher opposite to and touching the fluorescein, and either JOE, TET, TAMRA, ROX, or Texas red as the emitter fluorophore, a separation of 5 to 8 nucleotides between the two fluorophores provides optimal spacing. We find that with a five-nucleotide separation, FRET is substantial and predominates over quenching. We find that with a four-nucleotide separation there is substantial FRET but also substantially quenching, which is less preferred. The identity of the nucleotides in the spacer has little effect on the efficiency of energy transfer. The sequence of nucleotides in the spacer, however, should not form a hairpin that brings the harvester and emitter fluorophores to a quenching distance. Other kinds of spacers, such as alkyl spacers, can also be used.

We have discovered that, despite the presence of an emitter capable of receiving energy by transfer from the harvester, probes and primers according to this invention have suppressed emission when closed. We have discovered that suppression occurs when the quencher is in a quenching relationship with the harvester. We have also discovered that suppression occurs when the quencher is in a quenching relationship with the emitter. The mechanism or mechanisms by which suppression occurs are not understood. Nonetheless, as we show in the Examples below, fluorescence of the harvester is suppressed substantially in both cases, and at the same time fluorescence of the emitter is maintained at a low level, so that, when the probe or primer opens, fluorescence of the emitter increases detectably.

Any fluorophore that has strong absorption in the wavelength range of the available monochromatic light source can be used as the harvester fluorophore. For example, when an argon laser emitting blue light (488 nm) or a blue light emitting diode is used as the excitation source, fluorescein can serve as an excellent harvester fluorophore. Another harvester fluorophore that is efficient in the blue range is 3-($\epsilon$-carboxy-pentyl)-3'-ethyl-5,5'-dimethyloxacarbocyanine (CYA) [Hung et al. (1996) Anal. Biochem. 243:15]. For these harvester fluorophores, the emitter fluorophores can be 2',7'-dimethoxy-4',5'-dichloro-6-carboxy-fluorescein (JOE), tetrachlorofluorescein (TET), N,N,N',N'-tetramethyl-6-carboxyrhodamine (TAMRA), 6-carboxy-X-rhodamine (ROX), Texas red, and a number of cyanine dyes whose absorption spectra share substantial spectral overlap with the emission spectrum of fluorescein and CYA. With sources of different wavelengths, fluorphores may be selected to absorb and emit anywhere along the spectrum from ultraviolet to infrared. Compound fluorophores such as those described in Lee et al. (1997) can be used as a fluorophore.

Fluorophores and the quencher can be added to the probe by functionalization of the appropriate building blocks (e.g., deoxyribonucleotides) such that the fluorophores will be present on the building blocks prior to the formation of the probe, or they may be conjugated to the probe after formation, as appropriate. Various chemistries known to those of average skill in the art can be used to ensure that the appropriate spacing between the two fluorophores is obtained. In addition fluorophore phosphoramidites, for example a fluorescein phoshoramidite, can be used in place of a nucleoside phosphoramidite. A nucleotide sequence that contains such a substitution is considered to be an "oligonucleotide" as that term is used in this disclosure and in the appended claims, despite the substitution.

The fluorophores and the quencher can be attached via alkyl spacers to different positions on a nucleotide. The labels can be placed at internal or terminal locations in the oligonucleotide, using commonly available DNA synthesis reagents. The labels can also be placed at internal positions in oligonucleotides by substituting a nucleotide linked to a fluorophore moiety during synthesis. Although, commonly available spacers that employ alkyl chains of several carbons (Glen Research) can be used successfully, the degree of quenching and the extent of energy transfer can be further optimized by varying the length of the spacers.

Wavelength-shifting molecular beacon probes and hairpin primers according to this invention can be characterized by comparing their fluorescence to corresponding open conventional molecular beacon probes or hairpin primers having only the harvester fluorophore or only the emitter fluorophore. Wavelength-shifting probes and primers, when closed, (a) have harvester emission substantially suppressed as compared to corresponding open, harvester-only probes or primers similarly excited, and (b) have emitter emission substantially lower than emitter-only probes or primers excited at the emitter's excitation maximum. Wavelength-shifting probes and primers, when open, (c) still have harvester emission substantially suppressed as compared to corresponding open, harvester-only probes or primers similarly excited, and (d) have emitter emission both substantially higher than the emitter emission when closed and substantially higher than corresponding open, emitter-only probes or primers excited at the harvester's excitation maximum.

Harvester emission suppression is measured against emission from the open conformation of a corresponding conventional molecular beacon probe or hairpin primer labeled only with the harvester and quencher. Alternatively, a wavelength-shifting probe or primer according to this invention may be digested by incubation with DNAse I, which separates the label moieties and permits the harvester to fluoresce unhindered. Either of the foregoing can be used to obtain the magnitude, or intensity, of the harvester moiety against which harvester suppression is measured. By "substantially suppressed" we mean that the intensity of fluorescence of the harvester at its emission maximum is at least forty percent, preferably at least fifty percent, and more preferably at least sixty percent lower than either above standard against which it is measured.

Emitter emission when the probe or primer is in the closed conformation can be measured against emission from the open conformation of a corresponding conventional molecular beacon probe or hairpin primer that is emitter-quencher labeled and excited at the excitation maximum of the emitter. It should be substantially lower. Here again, by "substantially lower" we mean the intensity of fluorescence of the emitter at its emission maximum is at least forty percent, preferably at least fifty percent and more preferably at least sixty percent lower than the standard against which it is measured. This ensures that the emitter is not fluorescing maximally or close to maximally when the probe or primer is closed, permitting a detectable increase when the probe opens. In preferred embodiments that are "dark" when closed, there is little to no fluorescence at the emitter's wavelength, by which we mean that the emission is at least eighty percent lower than the above standard. It is a characteristic of probes and primers according to this invention that, when stimulated at a wavelength appropriate for the harvester, emission at the emitter's emission maximum increases detectably when the probe or primer opens. While an increase of twenty percent is generally a detectable increase, it is preferred that the increase be at least a factor of two, more preferably at least a factor of four. In preferred embodiments that are "dark" when closed, there is an increase of at least a factor of four and most preferably a factor of at least eight. These attributes, and other attributes that may be attractive for particular applications, are described in the Examples that follow.

EXAMPLES

Several of wavelength-shifting molecular beacon probes of varying constructions were prepared and tested. The following synthesis methods apply to the probes described in these Examples.

Conventional molecular beacon probes and wavelength-shifting probes according to this invention were synthesized. Labels were attached to the probe sequences either during automated synthesis or by post-synthetic reactions which have been described before [Tyagi and Kramer (1996)]. The quenchers were introduced to the oligonucleotides by any of he following three methods: a controlled-pore glass column was used to introduce a 4-dimethylaminoazobenzene-4'-sulfonyl moiety (DABSYL) at the 3' end of the oligonucleotides during automated synthesis; a succinimidyl ester of 4-(4'-dimethylaminophenylazo)benzoic acid (DABCYL) was used when the site of attachment was a primary amino group; and 4-dimethylaminophenylazophenyl-4'-maleimide (DABMI) was used when the site of attachment was a sulphydryl group. Fluorescein was introduced at internal locations in the DNA, either using a fluorescein phosphoramadite that replaces a nucleoside with fluorescein, or by using a fluorescein dT phosphoramadite that introduces a fluorescein moiety at a thymidine ring via a spacer. To link a fluorescein moiety to a terminal location, iodoacetoamidofluorescein was coupled to a sulphydryl group. Tetrachlorofluorescein (TET) was introduced during automated synthesis using a 5'-tetrachloro-fluorescein phosphoramadite. Other reactive fluorophore derivatives and their respective sites of attachment were: the succinimidyl ester of 5-carboxyrhodamine-6G (RHD) coupled to an amino group; an iodoacetamide of tetramethylrhodamine coupled to a sulphydryl group; an isothiocyanate of tetramethylrhodamine coupled to an amino group; or a sulfonylchloride of Texas red coupled to a sulphydryl group. During the synthesis of these multiply labeled probes the conjugated oligonucleotides were purified by high pressure liquid chromatography after each coupling step.

Example 1

Testing Probe Constructs

In the series of nine probes described in this example, DABSYL was utilized as the quencher, fluorescein as the harvester and TMR as the emitter. The oligonucleotide sequences of the probes are shown below. The sequences that participate in the formation of a stem duplex are underlined. Internally placed fluorophores are indicated by name only. For example, "fluorescein" refers to a fluorophore moiety that substitutes for a nucleotide in the oligonucleotide. Internally placed fluorophores indicated by T-names, for example, "(T-fluorescein)", refer to a thymidine nucleotide having the fluorophore attached to the thymidine ring via an alkyl spacer.

```
Probe 1
TMR-5'-TTTTT-fluorescein-CCACGCTTGTGGGTCAACCCCGTGG-3'-DABSYL         SEQ ID NO: 1

Probe 2
TMR-5'-TTTTT-fluorescein-CCACGCTTGTGGGTCAACCCCGTGGTTT-3'-DABSYL      SEQ ID NO: 2

Probe 3
TMR-5'-CCACGT-fluorescein-TCTTGTGGGTCAACCCCGTGG-3'-DABSYL            SEQ ID NO: 3

Probe 4
TMR-5'-CCGG(T-fluorescein)CCGCTTGTGGGTCAACCCGACCGG-3'-DABSYL         SEQ ID NO: 4

Probe 5
TMR-5'-TTCC(T-fluorescein)GGCCGCTTGTGGGTCAACCCGCCAGG-3'-DABSYL       SEQ ID NO: 5

Probe 6
TMR-5'-TTTT(T-fluorescein)GCGGCCGCTTGTGGGTCAACCCGCCGCA-3'-DABSYL     SEQ ID NO: 6

Probe 7
TMR-5'-CACACG(T-fluorescein)CCTGCCGCTTGTGGGTCAACCCGCAGG-3'-DABSYL    SEQ ID NO: 7

Probe 8
TMR-5'-CAGCACACG(T-fluorescein)CGCGCGCTTGTGGGTCAACCCCGCGA-3'-DABSYL  SEQ ID NO: 8

Probe 9
5'-(T-fluorescein)CAGCACACG(T-TMR)CGCGCGCTTGTGGGTCAACC              SEQ ID NO: 9
CCGCGA-3'-DABSYL For comparative purposes a conventional fluorescein-
DABSYL molecular beacon probe was also synthesized and
tested. Its sequence is shown below.

Probe 11
fluorescein-5'-CCACGCTTGTGGGTCAACCCCGTGG                             SEQ ID NO: 10
```

The probes were tested by subjecting them to an excitation source having a wavelength of 491 nm, in a Photon Technology International QuantaMaster spectrofluorometer, both in the absence of target (closed configuration) and in the presence of excess target (open configuration). Emission spectra were obtained from 500 to 650 nm, that is, across a range that includes the emission of both fluorescein and TMR. Results for probes 1–9 are presented in FIGS. 6–14, respectively. Each figure includes fluorescence intensities for open and closed probes. Spectra of samples without target are labeled 61, 71, . . . , 141, and spectra of samples with target are labeled 62, 72, . . . , 142.

Probe 1 is a preferred embodiment of this invention. It has a quencher, in this case DABSYL, terminally attached to one arm, namely, the 3'-terminus of the probe. It has a harvester, in this case fluorescein, in the 5' arm positioned opposite, in this case directly opposite, the quencher when the probe is closed. It has an emitter, in this case TMR, at the terminus of the 5' arm, five nucleotides beyond the fluorescein. Those five nucleotides are an extension of the 5' arm beyond the stem duplex. In this embodiment the harvester and quencher are in the most preferred quenching relationship, that is, they touch.

Figure 6:
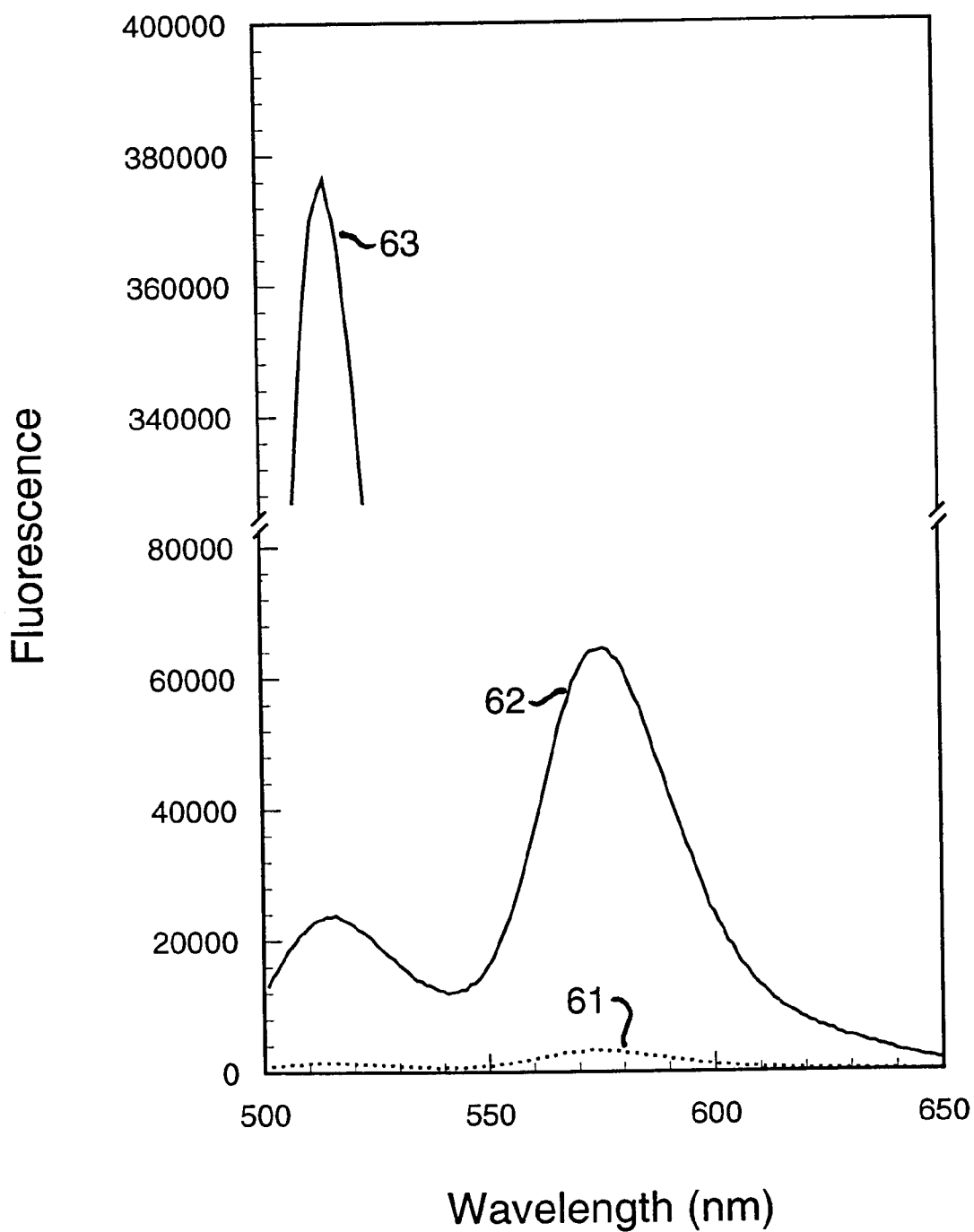
FIG. 6 is a graph of fluorescence of Probe 1, a probe according to this invention, and a fluorescein-labeled conventional molecular beacon probe.

FIG. 6 shows emission spectra for Probe 1. In the absence of target, trace 61, there was almost no fluorescence at the fluorescein maximum (515 nm) and very little fluorescence at the TMR maximum (575 nm); that is, the probe was quite dark when closed. In the presence of target, trace 62, there was an 18-fold increase in fluorescence at 575 nm. FIG. 6 also includes trace 63, the emission spectrum of the open, corresponding molecular beacon Probe 11. Because fluorescein emits so strongly as compared to other fluorophores, the vertical scale of FIG. 6 is broken. A comparison of traces 51 and 52 at 515 nm with trace 63 (Probe 11) at that wavelength shows that fluorescein emission was very substantially suppressed in both configurations of Probe 1, even though there was a modest amount of fluorescein emission in the open configuration. In the closed conformation the harvester suppression was greater than ninety-nine percent; in the open conformation, greater than ninety percent. The shape of spectrum 62 remained similar to the shape of spectrum 61. These results demonstrate that Probe 1 shifted emission towards the red as compared to Probe 11.

FIGS. 7–14, unlike FIG. 6, are normalized. The maximum emission when the probe is open is set at 1.0 on the vertical axis. The remaining peaks are fractions of that emission. FIGS. 7–14 do not include a trace for a corresponding fluorescein-labeled molecular beacon probe. However, by reference to FIG. 6 it can be appreciated that a fluorescein-labeled molecular beacon probe, when open, has an emission intensity that would be from 3.0 to 6.0 on the vertical scale of FIGS. 7–14. Substantial harvester suppression can be discerned from the fact that no fluorescein peak is even twice the intensity of the emitter peak when any of the probes is open.

Figure 7:
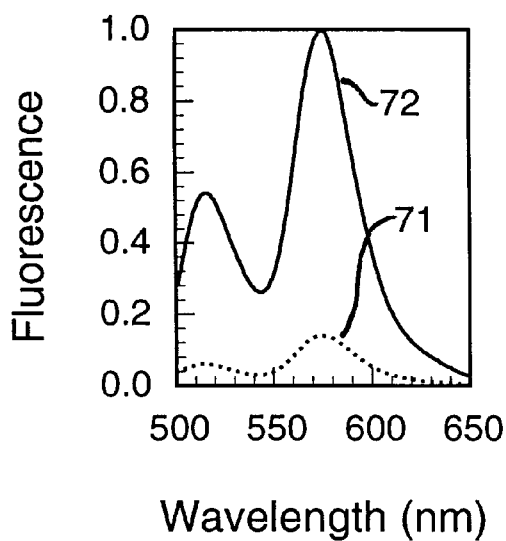
FIG. 7 is a graph of fluorescence of Probe 2, a probe according to this invention.

FIG. 7 shows the emission spectra of Probe 2. Probe 2 differs from Probe 1 in the position of DABSYL when the Probe is closed. In Probe 2 the 3' end of the probe was extended three nucleotides beyond the stem, moving the quencher to a point intermediate the two fluorophores on the other arm. In the open configuration, trace 72, the spectrum is essentially the same as for Probe 1, as expected. In the closed configuration, trace 71, there was very little fluorescence at either 515 nm or 575 nm, although slightly more then for Probe 1. Probe 2 was quenched quite effectively and was nearly dark when closed. Effective quenching of Probe 2 is not due to FRET.

Figure 8:
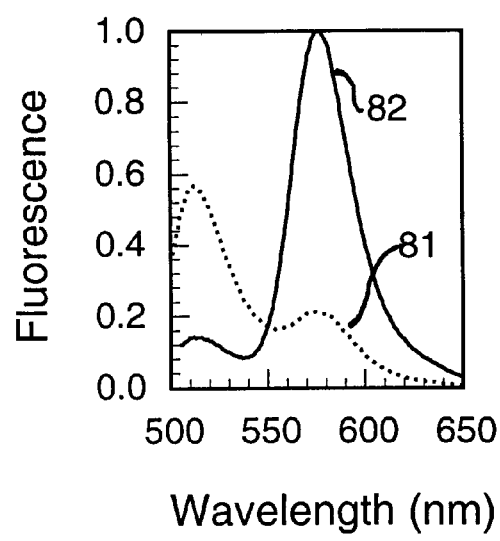
FIG. 8 is a graph of fluorescence of Probe 3, a probe according to this invention.

FIG. 8 shows the emission spectra of Probe 3. Probe 3 is somewhat reversed from Probe 1 in that a 5' terminal TMR, the emitter, is directly opposite from DABSYL across the stem duplex when the probe is closed. The fluorescein is located inboard from the stem duplex. There is a six-nucleotide separation between the two fluorophores. Spectra 81 and 82 show that Probe 3 exhibited a reversal of color when it opened, which may be useful in particular applications. In the absence of target there was appreciable fluorescence at 515 nm (albeit substantially suppressed), more than double the fluorescence at 575 nm. When Probe 3 opened, however, the opposite was found: fluorescence at 515 nm dropped by more than half, while fluorescence at 575 nm increased by a factor of 4.8. Thus, the color of the probe's fluorescence changed due to the presence of target. Probe 3 was not dark when closed.

Figure 9:
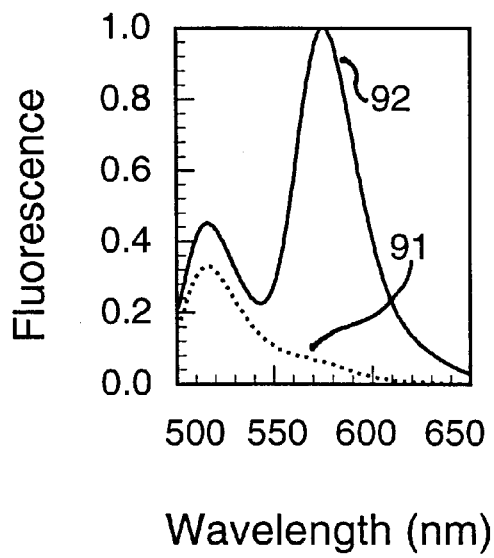
FIG. 9 is a graph of fluorescence of Probe 4, a probe according to this invention.
Figure 10:
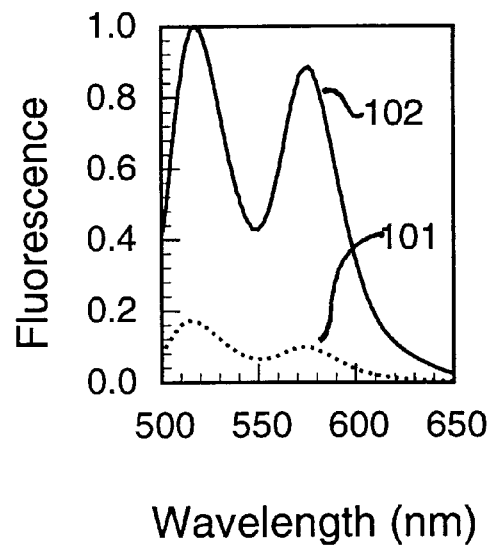
FIG. 10 is a graph of fluorescence of probe 5, a probe according to this invention.
Figure 11:
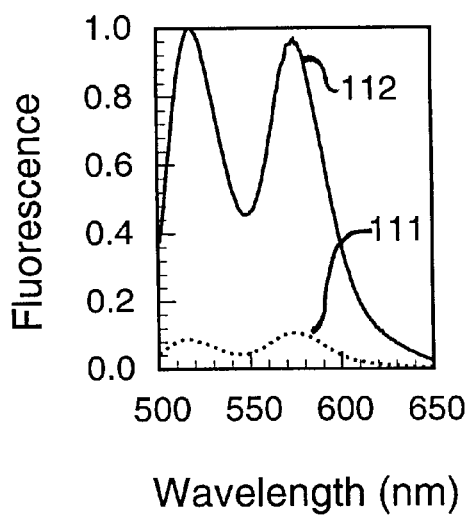
FIG. 11 is a graph of fluorescence of Probe 6, a probe according to this invention.
Figure 12:
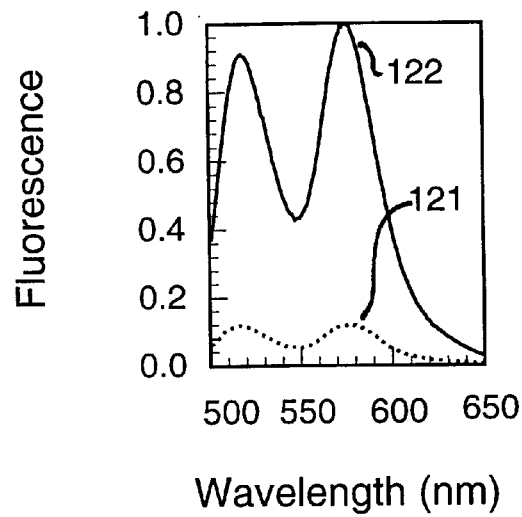
FIG. 12 is a graph of fluorescence of Probe 7, a probe according to this invention.
Figure 13:
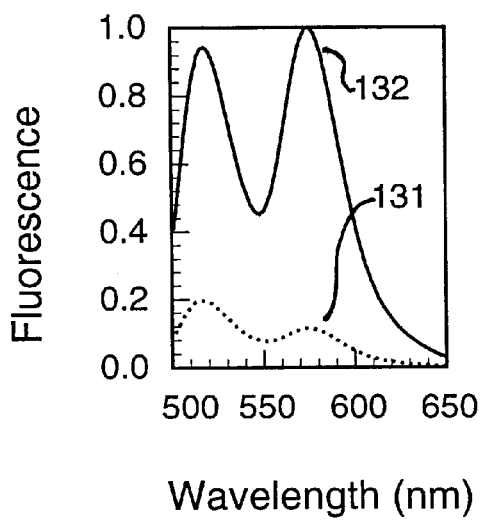
FIG. 13 is a graph of fluorescence of Probe 8, a probe according to this invention.

FIG. 9 shows the emission spectra of Probe 4, which is similar to Probe 3 in the placement of the TMR and DABSYL moieties at the end of the stem. Fluorescein is located inboard from TMR, but is located in the stem and attached to a thymidine nucleotide. In the closed configuration Probe 4 was better quenched than Probe 3 at 515 nm and had a lower fluorescence at 575 nm. However, the fluorescence intensity of Probe 4 did not decrease at 515 nm when it opened. It continued to have a modest, suppressed fluorescein emission. Because of its lower fluorescence at 575 nm when closed, as compared to Probe 3, its increase at 575 nm upon opening was three-fold better, namely, a factor of 16.0.

FIGS. 10–13 show the emission spectra of Probes 5–8, respectively. These constructions, when closed, all showed substantial quenching at 515 nm and low signal at 575 nm. When open each had an intensity increase at 575 nm greater than a factor of eight. When open, each had a fluorescein emission that, while appreciable, was substantially suppressed. All were dark when closed.

Figure 14:
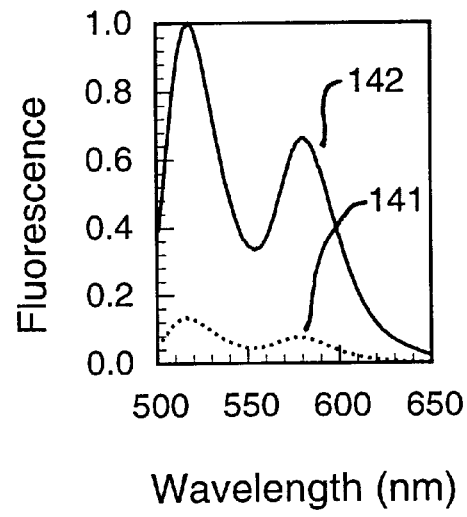
FIG. 14 is a graph of fluorescence of Probe 9, a probe according to this invention.

FIG. 14 shows the emission spectra for Probe 9. When Probe 9 was closed, fluorescein emission was very substantially suppressed. When open, fluorescence at 575 nm increased by more than a factor of eight, but suppression of fluorescein was only marginally substantial. While Probe 9 might be expected to have an emission spectrum when open that is very similar to the emission spectrum of Probe 8 when open, a difference was found in the relative intensities of the fluorescein and TMR peaks. Probe 9 had a smaller TMR peak relative to the fluorescein peak. This indicates that the efficiency of FRET between fluorescein and TMR was lower in Probe 9. Why then Probe 9 was better quenched is not clear. Perhaps the nature of the TMR was altered by its association with DABSYL in the closed configuration.

Example 2

Assays

Two additional probes were prepared, as follows:

```
Probe 12
Texas red-5'-CCACGCTTGTGGGTCAACCCCGTGG-3'-DABSYL           SEQ ID NO: 10

Probe 13
Texas red-5'-TTTTT-fluorescein-CCACGCTTGTGGGTCAACCCCGTGG-3'-    SEQ ID NO: 1
DABSYL
```

Probe 12 was a conventional molecular beacon probe terminally labeled with Texas red and DABSYL. It had the same nucleotide sequence as Probe 11, a conventional molecular beacon probe terminally labeled with fluorescein and DABSYL. Probe 13, on the other hand, is a wavelength-shifting molecular beacon probe according to a preferred construction (similar to Probe 1). Either Probe 11, Probe 12 or Probe 13 was added at the beginning of a PCR reaction to a test sample and to a control. The test samples were initiated with target. A reaction initiated with no target served as the control in each case. Each amplification included cycles of PCR in an Applied Biosystems 7700 PRISM spectrofluorometric thermal cycler. The light source in the instrument was an argon laser having a wavelength of 488 nm. Emission of each conventional molecular beacon probe was measured during the annealing phase of each cycle in the emission range of its fluorophore, fluorescein (Probe 11) or Texas red (Probe 12). Emission of the wavelength-shifting molecular beacon probe, Probe 13, was measured in the emission range of the emitter fluorophore, Texas red. The results are presented in FIGS. 2–4 and have been discussed earlier in this application.

Wavelength-shifting probes according to this invention may be used for detection in situ and in vivo, that is, in living cells. The difference in wavelength between the excitation maximum of the harvester and the emission maximum of the emitter, the Stokes shift of the probes, is larger than conventional probes. This is particularly advantageous detection when a microscope is used to monitor nucleic acids in biological samples. First, microscopes typically utilize a broad wavelength light source rather than a precise, single-wavelength light source. Second, biological samples have natural autofluorescence characterized by a small Stokes shift. Both of the foregoing characteristics contribute to background, which is avoided by wavelength-shifting probes. In certain assays probes may encounter degrading nucleases. Probe 1 illustrates a particular benefit of wavelength-shifting probes in such circumstances. If Probe 1 binds to target, red fluorescence results. However, if Probe 1 is degraded, green fluorescence results. One can see from FIG. 6 that degradation, by separating the harvester from the emitter, will restore fluorescein peak 63, which is stronger than TMR peak 62. Thus, one can see from the fluorescence whether or not degradation is occurring.

We note that it is of no consequence whether or not most probes according to this invention, Probe 13 for example, are cleaved by the polymerase during amplification, so long as cleavage does not occur between the harvester and the emitter. Where cleavage is found to occur during amplification, one could avoid using an embodiment in which either or both of the harvester and emitter moieties are in the probe-target hybrid, if that is found to lead to significant cleavage between the two of them. One could also use modified nucleotides, such as 2'-O-methylribonucleotides.

Example 3

Multiplex Assay

A multiplex assay is an assay utilizing at least two probes to test for at least two possible targets in the same sample. Multiple probes according to this invention for different targets can be used, and they can be used in a mixture with other probes. This example demonstrates the principle and also demonstrates allele discrimination. Wavelength-shifting molecular beacon Probe 13 was utilized as one probe. Another probe, Probe 14, was synthesized for use as a second probe:

```
Probe 14                                   SEQ ID NO: 11
fluorescein-5'-CCACGCTTGTCGGTCAACCCCGTGG-3'-DABSYL
```

Probe 14 is a conventional molecular beacon probe terminally labeled with fluorescein and DABSYL. The nucleotide sequence of Probe 14 differed from the nucleotide sequence of Probe 13 by a single nucleotide in the target complement sequence in the loop. A perfectly complementary target was synthesized for each probe. The perfect target for Probe 14 differed from the perfect target for Probe 13 by a single nucleotide.

Both probes were added to four PCR reaction mixes: a negative control containing no target, a sample containing the target perfectly complementary to Probe 14, a sample containing the target perfectly complementary to Probe 13, and a sample containing both of the targets in equal amounts. In each instance where any target was present, the total amount of target or targets was the same, about 200,000 copies.

Thermal cycling and fluorescence emission reading was as described in Example 2. The results are presented in FIG. 15 (no target), FIG. 16 (target perfectly complementary to Probe 14), FIG. 17 (target perfectly complementary to Probe 13), and FIG. 18 (both targets). The emissions in the fluorescein range, traces 151, 161, 171 and 181, are presented as dotted lines, and the emissions in the Texas red range, traces 152, 162, 172 and 182, are presented as solid lines.

Figure 15:
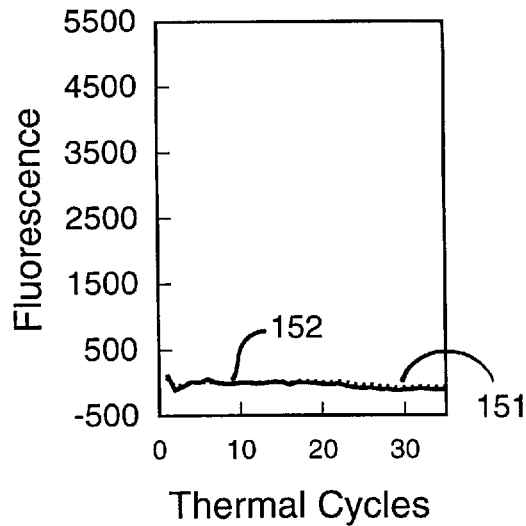
FIG. 15 is a graph of fluorescence of Probe 14, a conventional molecular beacon probe, and Probe 13, a wavelength-shifting probe according to this invention during a PCR amplification in which no target for either probe was present.
Figure 16:
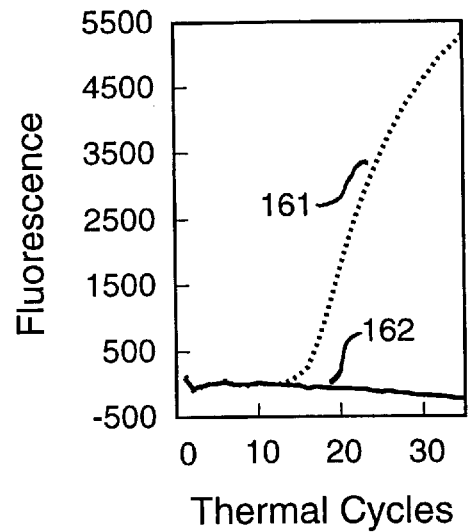
FIG. 16 is a graph of fluorescence of Probe 14 and Probe 13 during a PCR amplification in which target for Probe 14 was amplified.
Figure 17:
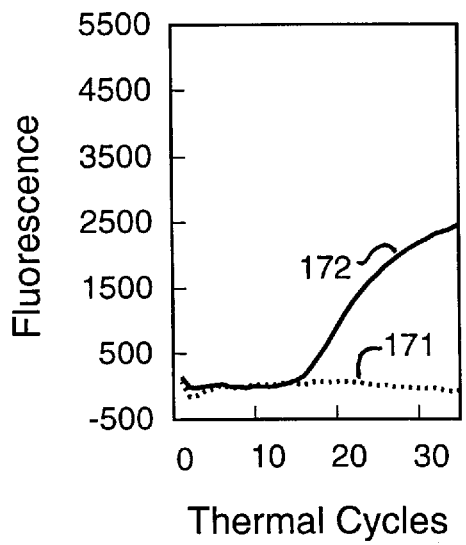
FIG. 17 is a graph of fluorescence of Probe 14 and Probe 13 during a PCR amplification in which target for Probe 13 was amplified.
Figure 18:
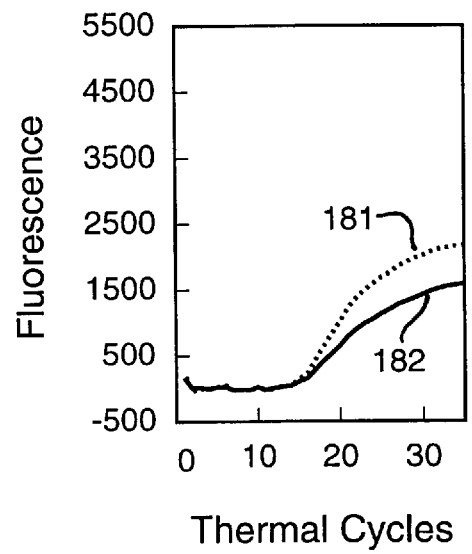
FIG. 18 is a graph of fluorescence of Probe 14 and Probe 13 during a PCR amplification in which targets for both Probe 14 and Probe 13 were amplified.

FIG. 15 shows that there was no fluorescence in the absence of target: both probes were dark when not hybridized to target. FIG. 16 shows high fluorescence in the fluorescein range caused by perfectly matched target for Probe 14, the fluorescein-labeled conventional molecular beacon probe. FIG. 16 also shows no fluorescence in the Texas red range, demonstrating that Probe 13 was an allele-discriminating probe that was sensitive to a single base-pair mismatch. FIG. 17 shows moderately high fluorescence in the Texas red range caused by perfectly matched target for Probe 13, a wavelength-shifting molecular beacon probe. FIG. 17 also shows no fluorescence in the fluorescein range, demonstrating that Probe 14 was an allele-discriminating probe that was sensitive to a single base-pair mismatch. FIG. 18 shows moderately high fluorescence in both ranges, which should occur because the amount of each target was one-half the total amount. In FIG. 18 the emission level in the Texas red range was 76% of the emission level in the fluorescein range. This is greatly improved compared to what would have occurred with a Texas red-labeled conventional molecular beacon probe stimulated at 488 nm, as FIG. 3 demonstrates, because the signal in the Texas red range would have been only 3% of the emission in the fluorescein range. Whereas a Texas red conventional molecular beacon is not generally suitable for multiplexing with a fluorescein-labeled conventional molecular beacon, a wavelength-shifting molecular beacon with a Texas red emitter is quite satisfactory for such multiplexing.

Example 4

Measuring the Characteristics of Wavelength-Shifting Probes

Probe 1, which is wavelength-shifting molecular beacon probe according to this invention having TMR as the emitter, was compared to several probes that were identical except for the emitter fluorophore. Three other fluorophores, tetrachlorfluorescein (TET), rhodamine 6G (RHD) and Texas red were utilized. When compared to their conventional molecular beacon counterparts using a 488 nm excitation source, the fluorescence of the wavelength-shifting probes in the open conformation was a much higher percentage of the maximum achievable fluorescence intensity than the corresponding conventional molecular beacon probe would have achieved in the open conformation, if it has been stimulated at its maximum excitation wavelength. Whereas the conventional molecular beacon probes stimulated at 488 nm achieved one-third or less of that maximum, the wavelength-shifting probes achieved two-thirds or more.

Figure 19:
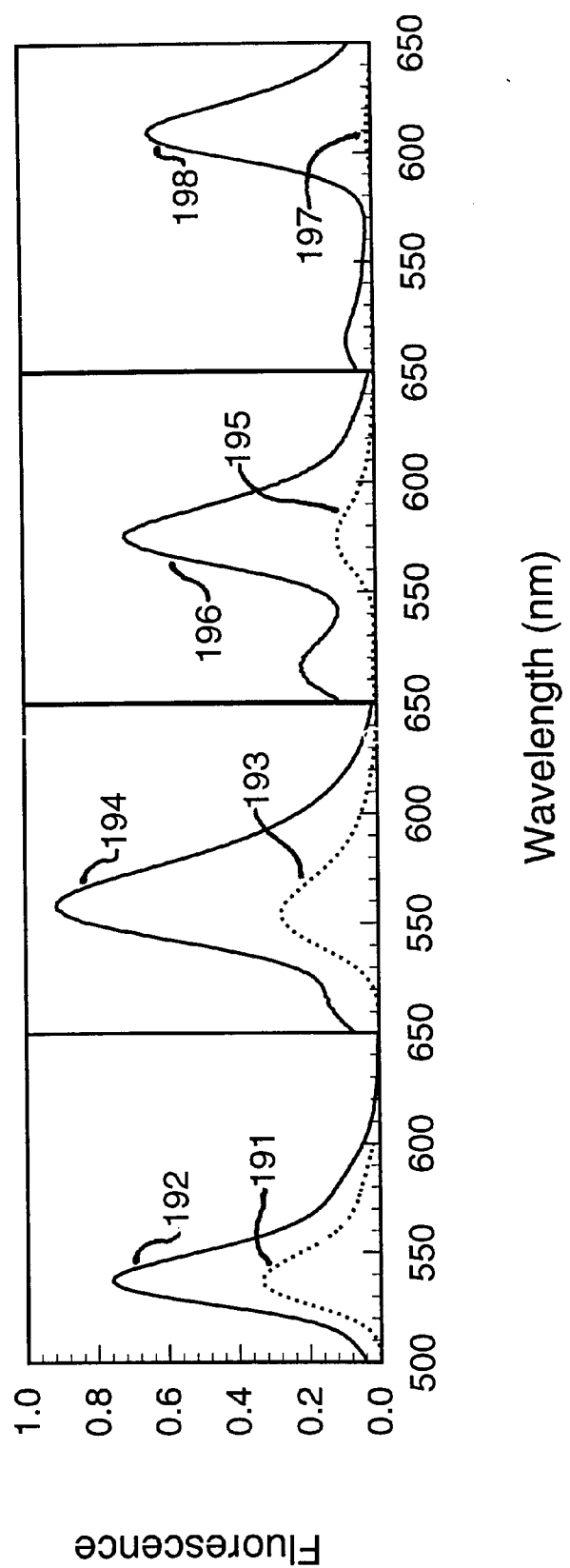
FIG. 19 is a graph of fluorescence of Probe 1, and the fluorescence of three other probes that are identical to Probe 1 except that they possess different emitter fluorophores.

Emission spectra for these probes are shown in FIG. 19, which illustrates the impact of the instant invention as the fluorescence color of the emitter flurophore departs more and more from the stimulation wavelength of the instrument. The fluorescence intensities are normalized, that is, presented as a fraction of the fluorescence achieved by stimulating the emitter directly at its maximum excitation wavelength. Curves 191 and 192 are the normalized emission spectra for a TET-labeled conventional molecular beacon probe and a corresponding wavelength-shifting molecular beacon probe having TET as the emitter, respectively. Curves 193 and 194 are the normalized emission spectra for an RHD-labeled conventional molecular beacon probe and a corresponding wavelength-shifting molecular beacon probe having RHD as the emitter, respectively. Curves 195 and 196 are analogous curves using TMR, and curves 197 and 198 are analogous curves using Texas red. Fluorescein is the harvester in all cases.

Curves for the conventional molecular beacon probes, that is, curves 191, 193, 195 and 197, show several things. First, the emission maxima shift to progressively longer wavelengths as the label is changed from TET to RHD to TMR to Texas red. Second, even for TET, the shortest wavelength fluorophore, excitation at 488 nm produces only about one-third of the emission achievable by excitation at the maximum absorption wavelength for TET, which is 522 nm. Third, the relative emission intensity falls off from one-third as the color of the fluorophore's fluorescence moves toward red, that is to longer wavelengths. For TMR, which has an emission maximum at 575 nm, only ten percent of the maximum achievable fluorescence intensity results. For Texas red, that percentage drops to three percent. Even with an expensive instrument having sophisticated emission detection, such as the Applied Biosystems 7700 PRISM, using TMR with a stimulating source of 488 nm is difficult, and using Texas red is not possible. With a less expensive instrument having unsophisticated detection, using either TMR or Texas red would not be possible. This markedly limits multiplexing possibilities and options, requiring use of fluorphores having closely spaced emission maxima, which are more difficult to resolve.

Curves for the wavelength-shifting probes according to this invention, that is, curves 192, 194, 196 and 198, also show several things. First, in every case there is increased emission intensity as compared to the corresponding conventional molecular beacon probe. Second, the relative intensities remain very high, about sixty-five percent, as one moves all the way to Texas red. Each of these probes is suitable for use with unsophisticated, less expensive instruments. Third, the amount of improvement over the corresponding conventional molecular beacon probe is greatest for the longest wavelength emitters, TMR and, especially, Texas red. Such marked improvement is significant even for use with an expensive instrument having sophisticated detection. Fourth, fluorescein emission is greatly suppressed. Referring to FIG. 6, one sees that fluorescein is perhaps the brightest fluorophore, roughly five times as bright as Probe 1, a wavelength shifting probe according to this invention. The emission of a corresponding conventional fluorescein molecular beacon probe would be off the scale of FIG. 19. Its intensity would be at least triple the maximum, "1.0", of the vertical axis.

Figure 20:
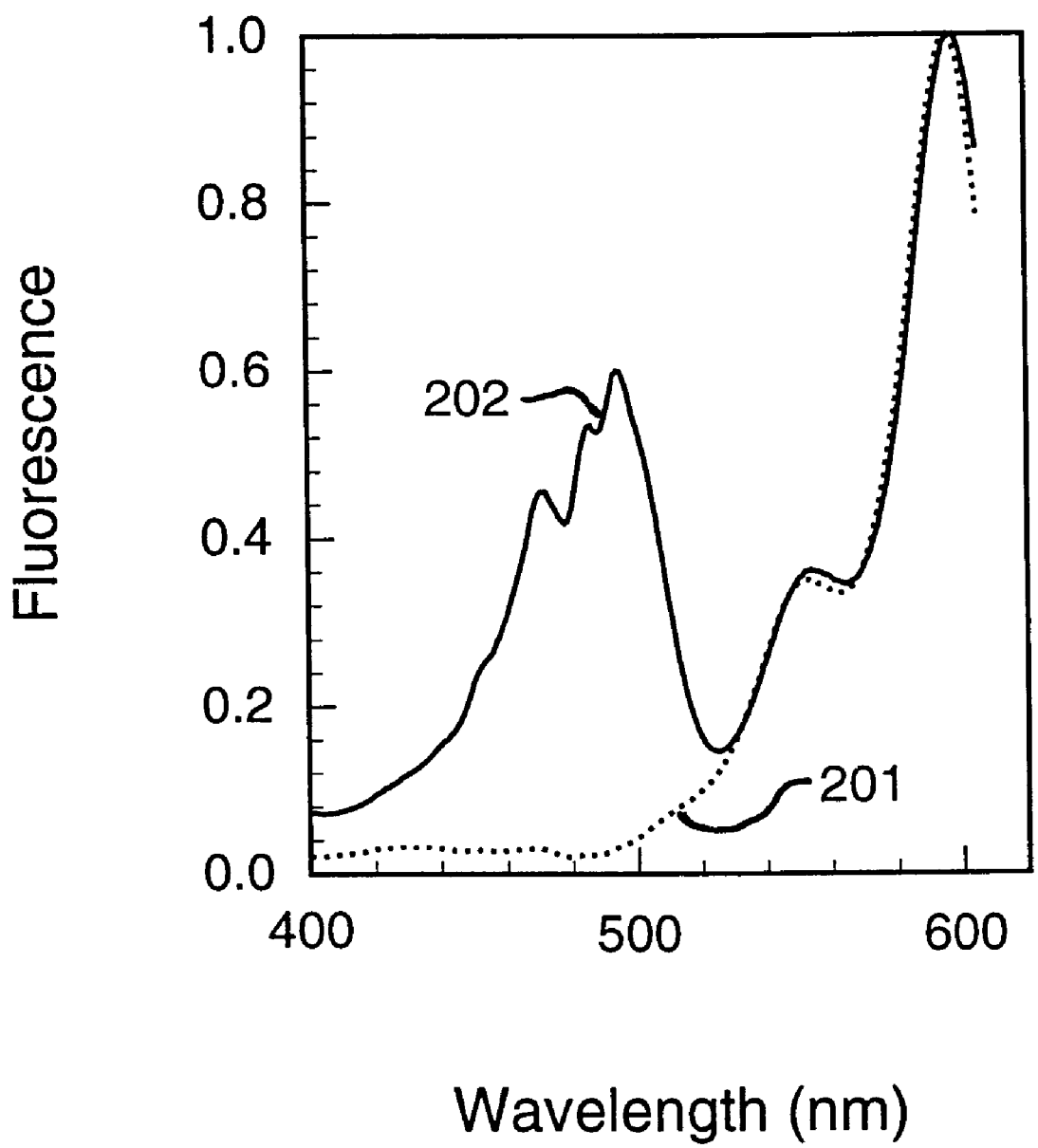
FIG. 20 is a graph of the fluorescence of Probe 1 substituted with a Texas-red emitter, measured at 610 nm and plotted as a function of excitation wavelength.

The changed nature of probes according to this invention is graphically illustrated by considering their excitation spectra. FIG. 20 compares the excitation spectrum of the Texas-red wavelength-shifting molecular beacon described above in this example and the corresponding Texas-red conventional molecular beacon probe. To obtain an excitation spectrum, the spectrofluorometer was set to read emission at 610 nm, the maximum for Texas red, as the excitation wavelength was increased progressively from 400 to 600 nm. Curve 201 for the conventional probe shows strong emission when the excitation wavelength reached 590 nm, the excitation maximum for Texas red. At 488 nm excitation almost no emission occurs. On the other hand, curve 202 for the wavelength-shifting shows not only the peak at 590 nm, but also a second strong peak at 488 nm. The probe has twin excitation ranges, both of which lead to emission at the wavelength of 610 nm.

Example 5

Wavelength-Shifting Primers

As stated earlier, a wavelength-shifting molecular beacon probe whose 3'arm sequence is complementary to the target can serve as a primer. However, it is not required that the loop of a hairpin primer be complementary to the target, because specificity can be obtained via an extension of the 3'arm, which creates a priming region. Conventional hairpin primers for PCR amplification can be synthesized and utilized, for example, according to the methods of Nazarenko et al. (1997). They can be modified according to the instant invention. Primer F described by Nazarenko et al. has the following sequence:

```
5'-6-fluorescein-CACCTTCACCCTCAGAAGG(T-DABCYL)GACC    SEQ ID NO: 12
AAGTTCAT-3'
```

In Primer F, 6-fluorescein was incorporated by using a 6-fluorescein phosphoramidite during synthesis. The T-DABCYL nucleotide was obtained by synthesizing with AminoModifier C6dT (Glen Research) and attaching DABCYL to the primary amino group. At least the first eighteen nucleotides from the 3' end were complementary to a target, a 172 base-pair segment of human prostate-specific antigen cDNA.

A primer embodiment according to this invention is made by modifying the sequence of Primer F in several respects. First, a phosphoramidite of fluorescein that can be inserted in the middle of a DNA chain (Glen Research) is utilized to introduce the harvester moiety. Second, six thymidine residues are added past the harvester toward the 5' end. Third, a Texas red moiety is introduced via a sulphydryl functionality. The primer according to this invention has the following sequence, with portions forming a stem duplex underlined):

Texas red-5'-TTTTT-fluorescein-<u>CACCTTC</u>ACCCTA<u>GAAGG</u>(T-    SEQ ID NO: 13
DABCYL)GACCAAGTTCAT-3'.

In the closed conformation, this primer has DABCYL opposite (with a single nucleotide offset) fluorescein across the stem duplex, with the Texas red on an extension. The construction is analogous to Probe 1 in Example 1. In the open conformation, the DABCYL is displaced from the fluorophores, and the two fluorophores (the harvester fluorescein and the emitter Texas red) are separated by seven nucleotides, a workable FRET separation. A PCR amplification of 30 cycles is carried out using this primer as one of the amplification primers. This construction functions as a wavelength-shifting hairpin primer. Wavelength-shifting hairpin primers of different colors can be multiplexed in amplification reactions. Nazarenko et al. utilized on "exo-minus" DNA polymerase, Pfu$^{exo-}$ DNA polymerase (Stratagene, USA), thereby avoiding possible cleavage during amplification. If cleavage is encountered during a particular amplification reaction using primers according to this invention, cleavage between the harvester and emitter moieties can be avoided as described in Example 2.

The Examples are presented for illustration and not as a limitation. Further embodiments will be apparent to workers in the art which fall within the following claims, which are intended as the measure of the invention.

What is claimed is:

1. A fluorescently labeled hairpin-forming oligonucleotide containing:

a) a fluorescent emitter moiety having an excitation spectrum and an emission spectrum including a maximum emission wavelength;

b) a fluorescent harvester moiety having an excitation spectrum including a maximum excitation wavelength, having an emission spectrum that overlaps the excitation spectrum of the emitter moiety and including a maximum emission wavelength, the emission of the harvester moiety at its maximum emission wavelength having a first magnitude when said harvester moiety is unquenched and stimulated at its maximum excitation wavelength; and c) a quencher moiety capable of quenching the fluorescence of at least one of the emitter moiety and the harvester moiety, said oligonucleotide having a closed conformation including a single-stranded loop and a stem duplex, wherein said quencher moiety is in a quenching relationship to at least one of said harvester and emitter moieties and wherein, when excited at the maximum excitation wavelength of the harvester moiety, emission at the maximum emission wavelength of the harvester moiety is substantially suppressed relative to said first magnitude and emission at the maximum emission wavelength of the emitter moiety has a second magnitude, and said oligonucleotide having an open conformation not including said stem duplex in which said quencher moiety is not in a quenching relationship with said harvester or said emitter moiety wherein, when excited at the maximum excitation wavelength of the harvester moiety, emission at the maximum emission wavelength of the harvester moiety is substantially suppressed relative to said first magnitude, energy is transferred from the harvester moiety to the emitter moiety, and emission at the maximum emission wavelength of the emitter moiety is detectably greater than said second magnitude.

2. The oligonucleotide of claim 1 wherein hybridization of said loop to a target sequence causes said oligonucleotide to assume its open conformation.

3. The oligonucleotide of claim 2 wherein said quencher moiety is selected from the group consisting of DABCYL and variants of DABCYL.

4. The oligonucleotide of claim 2 wherein, when said oligonucleotide is in its closed conformation, the emitter moiety is located on said oligonucleotide terminally to said stem duplex, the quencher and harvester moieties are located on said oligonucleotide in said stem duplex, and the harvester and quencher moieties are in a quenching relationship.

5. The oligonucleotide of claim 2 wherein, when said oligonucleotide is in its open conformation said emission at the maximum emission wavelength of the emitter is at least four times as great as said second magnitude.

6. The oligonucleotide of claim 2 wherein, when said oligonucleotide is in its closed conformation, said quencher and emitter moieties are located on said oligonucleotide in said stem duplex in a quenching relationship.

7. The oligonucleotide of claim 2 wherein at least one of said harvester and emitter moieties forms part of the nucleotide chain of said oligonucleotide.

8. The oligonucleotide of claim 2 wherein at least one of said harvester, emitter and quencher moieties is attached to said oligonucleotide through an alkyl linker.

9. The oligonucleotide of claim 2 wherein said oligonucleotide includes at least one of the group of modified nucleotides and modified linkages.

10. The oligonucleotide of claim 9 wherein said oligonucleotide comprises peptide nucleic acid (PNA).

11. The oligonucleotide of claim 9 wherein said oligonucleotide includes 2'-O-methylribonucleotides.

12. The oligonucleotide of claim 2 wherein one strand of said stem duplex is complementary to said target strand, whereby said oligonucleotide is capable of serving as a primer for a DNA polymerase.

13. The oligonucleotide of claim 1 wherein said oligonucleotide includes a terminal extension capable of serving as a priming region for a DNA polymerase when said oligonucleotide is in its closed conformation.

14. The oligonucleotide of claim 13 wherein said emitter moiety is located on said terminal extension and said quencher and harvester moieties are located on said oligonucleotide in said stem duplex.

15. The oligonucleotide of claim 13 wherein at least one of said harvester and emitter moieties forms part of the nucleotide chain of said oligonucleotide.

16. The oligonucleotide of claim 13 wherein at least one of said harvester, emitter and quencher moieties is attached to said oligonucleotide through an alkyl linker.

17. The oligonucleotide of claim 13 wherein said oligonucleotide includes at least one of the group of modified nucleotides and modified linkages.

18. A reagent kit comprising ingredients for a nucleic acid amplification, a detector probe that is an oligonucleotide according to claim 2, and instructions for carrying out said amplification reaction.

19. The kit of claim 18 wherein said amplification is selected from the group consisting of polymerase chain reaction (PCR), strand displacement amplification (SDA), transcription mediated amplification (TMA), ligase chain reaction (LCR), nucleic acid sequence based amplification (NASBA), rolling circle amplification, and amplification of RNA by an RNA-directed RNA polymerase.

20. The kit according to claim 18 wherein said oligonucleotide is designed to hybridize to a perfectly complementary target sequence but not to hybridize significantly to a sequence differing therefrom by at least one nucleotide.

21. The kit according to claim 18 wherein the emitter moiety is located on said oligonucleotide terminally to said stem duplex and the quencher and harvester moieties are located on said oligonucleotide in said stem duplex.

22. A reagent kit for an amplification reaction that includes at least one primer, comprising the ingredients for said amplification assay and instructions for carrying out said amplification assay, wherein said at least one primer is an oligonucleotide according to claim 13.

23. The kit according to claim 22 wherein said amplification reaction is selected from the group consisting of the polymerase chain reaction (PCR), strand displacement amplification (SDA), transcription mediated amplification (TMA), ligase chain reaction (LCR), nucleic acid sequence based amplification (NASBA), rolling circle amplification, and amplification of RNA by an RNA-directed RNA polymerase.

24. The kit according to claim 23 wherein said oligonucleotide includes 2'-O-methylribonucleotides.

25. A detection assay comprising adding to a sample that might contain a target strand at least one detector probe that is an oligonucleotide according to claim 2 and detecting fluorescence emission from said at least one probe's emitter moiety.

26. The assay according to claim 25 further comprising detecting fluorescence emission from said at least one probe's harvester moiety.

27. The assay according to claim 26 further comprising adding said at least one detector probe to a sample that does not contain said target strand and detecting fluorescence emission of said harvester and emitter moieties.

28. The assay according to claim 25 further comprising adding said detector probe to a sample that does not contain said target strand and detecting fluorescence emission of said at least one probe's emitter moiety.

29. The assay according to claim 25 wherein the emitter moiety is of said at least one probe located on said oligonucleotide terminally to said stem duplex and the quencher and harvester moieties are located on said oligonucleotide in said stem duplex.

30. The assay according to claim 25 wherein one of the harvester and emitter moieties of said at least one probe is a phosphoramidite derivative of a fluorophore that is incorporated in said oligonucleotide.

31. The assay according to claim 25 wherein said at least one probe comprises at least two probes, each having a different emitter moiety.

32. The assay according to claim 25, wherein said assay is selected from the group consisting of in situ and in vivo assays.

33. An amplification assay comprising adding to a sample that might contain a target strand the reagents to perform an amplification reaction selected from the group consisting of the polymerase chain reaction (PCR), strand displacement amplification (SDA), transcription mediated amplification (TMA), ligase chain reaction (LCR), nucleic acid sequence based amplification (NASBA), rolling circle amplification, and amplification of RNA by an RNA-directed RNA polymerase, and at least one detector probe according to claim 2 and detecting fluorescence emission from said at least one probe's emitter moiety.

34. The assay according to claim 33, wherein said assay is selected from the group consisting of in situ and in vivo assays.

35. The assay according to claim 33 further comprising detecting fluorescence emission from said at least one probe's harvester moiety.

36. The assay according to claim 35 further comprising adding said at least one detector probe to a sample that does not contain said target strand and detecting fluorescence emission of said at least one probe's harvester and emitter moieties.

37. The assay according to claim 33 further comprising adding said at least one detector probe to a sample that does not contain said target strand and detecting fluorescence emission of said at least one probe's emitter moiety.

38. The assay according to claim 33 wherein the emitter moiety is located on said oligonucleotide terminally to said stem duplex and the quencher and harvester moieties are located on said oligonucleotide in said stem duplex.

39. The assay according to claim 33 wherein one of the harvester and emitter moieties of said at least one probe is a phosphoramidite derivative of a fluorophore that is incorporated in said oligonucleotide.

40. The assay according to claim 33 wherein said at least one probe comprises at least two probes, each having a different emitter moiety.

41. The assay according to claim 33 wherein said oligoncleotide includes 2'-O-methylribonucleotides.

42. An amplification assay comprising an amplification reaction that includes at least one primer comprising the steps of adding to a sample that might contain a target strand the reagents to perform said amplification reaction, said reagents including at least one primer according to claim 12, and detecting fluorescence of said emitter moiety.

43. The assay according to claim 42, wherein said assay is selected from the group consisting of in situ and in vivo assays.

44. The amplification assay according to claim 42 wherein said at least one primer according to claim 12 comprises at least two primers.

45. An amplification assay comprising an amplification reaction that includes at least one primer comprising the steps of adding to a sample that might contain a target strand the reagents to perform said amplification reaction, said reagents including at least one primer according to claim 13, and detecting fluorescence of said emitter moiety.

46. The amplification assay according to claim 45 wherein said at least one primer according to claim 13 comprises at least two primers.

47. The amplification assay according to claim 45 further comprising detecting fluorescence emission from said harvester moiety.

48. The amplification assay according to claim 45 wherein the emitter moiety is located on said oligonucleotide terminally to said stem duplex and the quencher and harvester moieties are located on said oligonucleotide in said stem duplex.

49. The assay according to claim 45 wherein one of the harvester and emitter moieties of said at least one probe is a phosphoramidite derivative of a fluorophore that is incorporated in said oligonucleotide.

50. The assay according to claim 45 wherein said at least one probe comprises at least two probes, each having a different emitter moiety.

* * * * *